(12) United States Patent
Bruheim

(10) Patent No.: US 10,933,099 B2
(45) Date of Patent: Mar. 2, 2021

(54) COMPOSITIONS AND METHODS OF USING KRILL POWDER IN CARDIOVASCULAR REGULATION

(71) Applicant: RIMFROST TECHNOLOGIES AS, Fosnavåg (NO)

(72) Inventor: Inge Bruheim, Volda (NO)

(73) Assignee: RIMFROST TECHNOLOGIES AS, Fosnavag (NO)

( * ) Notice: Subject to any disclaimer, the term of this patent is extended or adjusted under 35 U.S.C. 154(b) by 354 days.

(21) Appl. No.: 15/873,389

(22) Filed: Jan. 17, 2018

(65) Prior Publication Data
US 2018/0207205 A1    Jul. 26, 2018

Related U.S. Application Data

(60) Provisional application No. 62/448,633, filed on Jan. 20, 2017.

(51) Int. Cl.
*A61K 35/612* (2015.01)
*A61P 9/12* (2006.01)

(52) U.S. Cl.
CPC .............. *A61K 35/612* (2013.01); *A61P 9/12* (2018.01)

(58) Field of Classification Search
CPC .. A61K 35/612; A61K 31/202; A61K 31/215; A61K 31/683; A61P 9/12; A61P 3/00; A61P 3/04; A61P 9/10
See application file for complete search history.

(56) References Cited

PUBLICATIONS

Berge K, et al "Chronic treatment with krill powder reduces plasma triglyceride and anandamide levels in mildly obese men" Lipids in Health and Disease, May 27, 2013, 12(78); doi:10.1186/1476-511X-12-78. (Year: 2013).*
Yuldashev S, "Blood lipids and body weight in patients with postinfarction cardiosclerosis in relation blood pressures" Meditsinskii Zhurnal Uzbekistana (1986), (12), 21-23 (abstract only.) (Year: 1986).*
Shimizu Y, et al "Triglycerides and blood pressure in relation to circulating CD34-positive cell levels among community-dwelling elderly Japanese men: a cross-sectional study" Environmental Health and Preventive Medicine, 2017, vol. 22 (No. 77), 7 pp; doi: 10.1186/s12199-017-0684-x. (Year: 2017).*
Daniells "First krill powder study shows potential for metabolic syndrome", Nutra, 12, Jun. 2013, 2 pages (Year: 2013).*
Searby L "Krill powder stability issues addressed: Study" Sep. 14, 2016, Nutra, 2 pages (Year: 2016).*
Nutrascience Innovations LLC, "Krill (Oil & Powder)" (online URL: nutriscienceusa.com/krill-oil-krill-powder/, accessed Apr. 27, 2020), 2 pages (Year: 2020).*
Yuldashev S, "Blood lipids and body weight in patients with postinfarction cardiosclerosis in relation blood pressures" Meditsinskii Zhurnal Uzbekistana (1986), (12), pp. 21-23. (Year: 1986).*
(2010) "Krill oil. Monograph," *Alternative Medicine Review* 15(1), 84-86.
Andersson, C. et al. (2014) "Long-term risk of cardiovascular events across a spectrum of adverse major plasma lipid combinations in the Framingham Heart Study," *American Heart Journal* 168(6), 878-883.e871.
Berge, K. et al. (2014) "Krill oil supplementation lowers serum triglycerides without increasing low-density lipoprotein cholesterol in adults with borderline high or high triglyceride levels," *Nutrition Research* 34(2), 126-133.
Bunea, R. et al. (2004) "Evaluation of the effects of Neptune Krill Oil on the clinical course of hyperlipidemia," *Alternative Medicine Review* 9(4), 420-428.
Calder, P. C. (1997) "n-3 polyunsaturated fatty acids and cytokine production in health and disease," *Annals of Nutrition & Metabolism* 41(4), 203-234.
Calder, P. C. (2002) "Dietary modification of inflammation with lipids," *Proceedings of the Nutrition Society* 61(3), 345-358.
Ciccone, M. M. et al. (2013) "Dietary intake of carotenoids and their antioxidant and anti-inflammatory effects in cardiovascular care," *Mediators of Inflammation* 2013, 782137.
Fassett, R. G. et al. (2012) "Astaxanthin in cardiovascular health and disease," *Molecules (Basel, Switzerland)* 17(2), 2030-2048.
Guerin, M. et al. (2003) "Haematococcus astaxanthin: applications for human health and nutrition," *Trends in Biotechnology* 21(5), 210-216.
Harris, W. S. (2007) "Omega-3 fatty acids and cardiovascular disease: a case for omega-3 index as a new risk factor," *Pharmacological Research* 55(3), 217-223.
Harris, W. S. et al. (2013) "Omega-3 fatty acids and cardiovascular disease: new developments and applications," *Postgraduate Medicine* 125(6), 100-113.
Hatanaka, a. et al. (2009) "Isolation and identification of antihypertensive peptides from antarctic krill tail meat hydrolysate," *Journal of Food Science* 74(4), H116-120.
Lee, J. K. et al. (2012) "Characterization of bioactive peptides obtained from marine invertebrates," *Advances in Food and Nutrition Research* 65, 47-72.
Li, K. et al. (2014) "Effect of marine-derived n-3 polyunsaturated fatty acids on C-reactive protein, interleukin 6 and tumor necrosis factor α: a meta-analysis," *PLoS ONE* 9(2), e88103.
Martínez-Maqueda, D. et al. (2012) "Antihypertensive peptides from food proteins: a review," *Food & Function* 3(4), 350-361.
Members, A. T. F. et al. (2013) "2013 ESH/ESC Guidelines for the management of arterial hypertension: The Task Force for the management of arterial hypertension of the European Society of Hypertension (ESH) and of the European Society of Cardiology (ESC)," *European Heart Journal* 34(28), 2159-2219.
Nielsen, N. S. et al. (2017) "Quality changes of Antarctic krill powder during long term storage," *European Journal of Lipid Science and Technology* 119(3), 1600085.
Oh, P. C. et al. (2014) "Omega-3 fatty acid therapy dose-dependently and significantly decreased triglycerides and improved flow-mediated dilation, however, did not significantly improve insulin sensitivity in patients with hypertriglyceridemia," *International Journal of Cardiology* 176(3), 696-702.

(Continued)

*Primary Examiner* — Aaron J Kosar
(74) *Attorney, Agent, or Firm* — Medlen & Carroll, LLP

(57) ABSTRACT

The present invention is related to the regulation of the cardiovascular system. In particular, to krill powder compositions and their administration to mammal for regulation of blood pressure.

17 Claims, 4 Drawing Sheets

(56) References Cited

PUBLICATIONS

Riccioni, G. et al. (2011) "Marine carotenoids and cardiovascular risk markers," *Marine Drugs* 9(7), 1166-1175.

Sadzuka, Y. et al. (2012) "Beneficial effects by intake of Euphausiacea pacifica on high-fat diet-induced obesity," *Biological & Pharmaceutical Bulletin* 35(4), 568-572.

Trepanowski, J. F. et al. (2012) "A 21-day Daniel fast with or without krill oil supplementation improves anthropometric parameters and the cardiometabolic profile in men and women," *Nutrition and Metabolism* 9(1), 82.

Von Schacky, C. (2011) "The Omega-3 Index as a risk factor for cardiovascular diseases," *Prostaglandins & Other Lipid Mediators* 96(1), 94-98.

Von Schacky, C. et al. (2007) "Cardiovascular benefits of omega-3 fatty acids," *Cardiovascular Research* 73(2), 310-315.

Wachira, J. K. et al. (2014) "n-3 Fatty acids affect haemostasis but do not increase the risk of bleeding: clinical observations and mechanistic insights," *British Journal of Nutrition* 111(9), 1652-1662.

* cited by examiner

COMPOSITIONS AND METHODS OF USING KRILL POWDER IN CARDIOVASCULAR REGULATION

FIELD OF THE INVENTION

The present invention is related to the regulation of the cardiovascular system. In particular, to krill powder compositions and their administration to mammal for regulation of blood pressure.

BACKGROUND

Krill powder can be produced as a reddish powder derived from Antarctic Krill (*Euphasia superba*). This krill powder has been determined to be rich in multiple bioactive ingredients including, but not limited to, fatty acids:eicosapentanoic acid (EPA, 20:5n-3) and docosahexanoic acid (DHA), phospholipids, protein and astaxanthin. Although it is not necessary to understand the mechanism of an invention, it is believed that long-chain n-3 polyunsaturated fatty acids are essential fatty acids for normal development. In addition EPA and DHA have been reported to have a variety of beneficial effects in cardiovascular diseases. Also other constituents in krill powder like marine peptides and astaxanthin have shown to have potential to reduce cardiovascular risk factors like blood pressure lowering (Hatakana et al. 2009) and protecting from lipid oxidation (Fasset & Coombes 2011, Riccione 2011 Ciccione 2013), respectively.

Thus, krill powder has been reported to have potential as a health properties owing ingredient in food area. However, randomized clinical trials on krill powder are scarce and thus there is a need to systematically collect data on its safety and tolerability in humans. Simultaneously it is of interest to pilot its effect on certain cardiovascular risk factors like blood pressure and serum lipoprotein lipids among others.

It is therefore a long felt need in the art to provide a safe and tolerable krill powder product to reduce blood pressure in slightly obese study subjects.

SUMMARY OF THE INVENTION

The present invention is related to the regulation of the cardiovascular system. In particular, to krill powder compositions and their administration to mammal for regulation of blood pressure.

In one embodiment, the present invention contemplates a method, comprising: a) providing; i) a patient exhibiting at least one prehypertensive symptom; and ii) an effective amount of a krill powder composition; b) administering said krill powder composition to said patient under conditions such that said at least one prehypertensive symptom is reduced. In one embodiment, the at least one prehypertensive symptom comprises a diastolic blood pressure ranging between approximately 86-90 mmHg. In one embodiment, the at least one prehypertensive symptom comprises a systolic blood pressure ranging between approximately 138-142 mmHg. In one embodiment, the reduced at least one prehypertensive symptom comprises an approximate 3% reduction in diastolic blood pressure. In one embodiment, the reduced at least one prehypertensive symptom comprises an approximate 5% reduction in systolic blood pressure. In one embodiment, the patient is overweight having a body mass index ranging between approximately 25.0 to 29.9. In one embodiment, the patient is obese having a body mass index ranging between approximately 30.0-39.9. In one embodiment, the patient is extremely obese having a body mass index in excess of 40.0. In one embodiment, the krill powder comprises between approximately 300-400 ppm fluoride. In one embodiment, the krill powder comprises a reddish color. In one embodiment, the effective amount of said krill powder remains stable over a one year period. In one embodiment, the conditions comprise an approximate 50% reduction in adverse events within said patient as compared to a subject not administered said effective amount of krill powder. In one embodiment, the conditions comprise no significant changes in said patient's laboratory measurements including, but not limited to, low density lipoprotein levels, high density lipoprotein levels, total cholesterol levels, and triglyceride levels. In one embodiment, the conditions comprise no significant changes in body weight of said patient. In one embodiment, the krill powder is rich in marine omega-3 phospholipids, proteins, peptides and astaxanthin. In one embodiment, the krill powder is Antarctic krill powder. In one embodiment, the Antarctic krill powder is *Euphanasia superba* krill powder.

In one embodiment, the present invention contemplates a product comprising a krill powder composition for use in a treatment of a patient comprising at least one prehypertensive symptom. In one embodiment, the at least one prehypertensive symptom comprises a diastolic blood pressure ranging between approximately 86-90 mmHg. In one embodiment, the at least one prehypertensive symptom comprises a systolic blood pressure ranging between approximately 138-142 mmHg. In one embodiment, the reduced at least one prehypertensive symptom comprises an approximate 3% reduction in diastolic blood pressure. In one embodiment, the reduced at least one prehypertensive symptom comprises an approximate 5% reduction in systolic blood pressure. In one embodiment, the patient is overweight having a body mass index ranging between approximately 25.0 to 29.9. In one embodiment, the patient is obese having a body mass index ranging between approximately 30.0-39.9. In one embodiment, the patient is extremely obese having a body mass index in excess of 40.0. In one embodiment, the krill powder comprises between approximately 300-400 ppm fluoride. In one embodiment, the krill powder comprises a reddish color. In one embodiment, the effective amount of said krill powder remains stable over a one year period. In one embodiment, the conditions comprise an approximate 50% reduction in adverse events within said patient as compared to a subject not administered said effective amount of krill powder. In one embodiment, the conditions comprise no significant changes in said patient's laboratory measurements including, but not limited to, low density lipoprotein levels, high density lipoprotein levels, total cholesterol levels, and triglyceride levels. In one embodiment, the conditions comprise no significant changes in body weight of said patient. In one embodiment, the krill powder is rich in marine omega-3 phospholipids, proteins, peptides and astaxanthin. In one embodiment, the krill powder is Antarctic krill powder. In one embodiment, the Antarctic krill powder is *Euphanasia superba* krill powder.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" or "approximately" as used herein, in the context of any of any assay measurements refers to +/−5% of a given measurement.

Abbreviations used in this application are as follows:
AE adverse event
ALAT alanine aminotransferase
apoA1 apolipoprotein A1
apoB apolipoprotein B
ASAT aspartate aminotransferase
BP blood pressure
BMI body mass index
° C. Celsius
CRF case report form
CVD cardiovascular disease
DHA docosahexaenoic acid
EPA eicosapentanoic acid
FA fatty acids
g gram/grams
h hour/hours
HDL high density lipoprotein
kg kilogram/kilograms
LDL low density lipoprotein
lp(a) lipoprotein (a)
m meter
MedDRA Medical Dictionary for Regulatory Activities
min minute/minutes
ml millilitre/milliliters
NA not applicable
ND not done
NK not known
p p-value
PL phospholipids
PT preferred term
PUFA polyunsaturated fatty acids
SAE serious adverse event
SD standard deviation
SOC system organ class
TG triglycerides
TNFα tumor necrosis factor alfa
TSH thyroid stimulating hormone
% percent As used herein, the term "adverse event" means any unfavourable and unintended sign, symptom or medical complaint and worsening of a pre-existing condition. Adverse events may be recorded at any time during the study period but does not include illnesses or pre-existing conditions found during the Pre-Screening or Screening Visits. Planned surgical operations are recorded, but are not considered adverse events. At each Visit during the study period all AEs either observed by the investigator, or reported by the subject spontaneously, may be recorded by the investigator and evaluated. Each AE may be described using at least one of the following parameters:
Description of event
Seriousness
Onset and stop of event
Severity
Relation to investigational product
Action taken
Outcome As used herein the term "clinical laboratory adverse event" refers to any clinical laboratory abnormality if the following conditions are met: i) the abnormality suggests a disease and/or organ toxicity; and ii) the abnormality is of such a severity which requires active management, i.e. change of dose, discontinuation of the krill powder, more frequent follow-ups, and/or diagnostic investigations. Homeostatic fluctuation in laboratory values which remain within provided reference values are not considered clinical laboratory adverse events.

As used herein, the term "serious adverse event" means at least one untoward medical occurrence that: i) results in death; ii) is life-threatening; iii) requires inpatient hospitalisation or prolongation of existing hospitalisation; iv) results in persistent or significant disability/incapacity; or v) is a congenital anomaly/birth defect. Generally, inpatient hospitalization includes an overnight admission, but pre-planned elective procedures are not to be reported as serious adverse events even if involving an overnight hospital admission.

As used herein, the term "life-threatening adverse event" means any event in which the subject or patient was at risk of death at the time of the event; it does not refer to an event in and of itself, which might have caused death if it were more severe.

As used herein, the term "severity assessment" refers to a medical evaluation of any type of adverse event.

As used herein, the term "mild severity assessment" means an adverse event comprising transient symptoms where there is no interference with the subject or patient daily activities and is deemed as medically acceptable by trained medical personnel.

As used herein, the term "moderate severity assessment" means an adverse event comprising marked symptoms where there is moderate interference with the subject or patient daily activities but is deemed medically acceptable by trained medical personnel.

As used herein, the term "severe severity assessment" means an adverse event comprising symptoms where there is considerable interference with the subject or patient daily activities and is deemed medically unacceptable by trained medical personnel.

As used herein, the term "causal" to krill powder means any adverse event that is related to the administration of krill powder to a subject or patient.

As used herein, the term "not causally related" to krill powder means any adverse event that is not related to the administration of krill powder to a subject or patient.

As used herein, the term "unlikely causally related" to krill powder means any adverse event for which an alternative explanation is more likely—e.g. concomitant product(s), concomitant disease(s), and/or relationship in time, suggests that it is not related to the administration of krill powder to subject or patient.

As used herein, the term "possibly causally related" to krill powder means any adverse event for which an alternative explanation—e.g. concomitant product(s), concomitant disease(s),—is inconclusive. The relationship in time is reasonable; therefore a causal relationship to the administration of krill powder to a subject or patient cannot be excluded.

As used herein, the term "probably causally related" to krill powder means any adverse event, which might be due to the administration of krill powder to a subject or patient. The relationship in time is suggestive (e.g. confirmed by dechallenge). An alternative explanation is less likely—e.g. concomitant product(s), concomitant disease(s).

As used herein, the term "definitely causally related" to krill powder means any adverse event due to the administration of krill powder to a subject or patient that cannot be reasonably explained by an alternative explanation, e.g. concomitant product(s), concomitant disease(s). The relationship in time is very suggestive (e.g. it is confirmed by dechallenge and rechallenge.)

As used herein, the term "case report form" (CRF) includes any form designed to record all the data produced by the performance of the study. Data obtained via subject diary may be transferred to the CRF as to the AE recording, concomitant medication, and krill powder ingestion compliance data.

The term "disintegrated material" as used herein refers to any biological material that has been subjected to a mechanical destruction and/or disruption that results in a composition having particle sizes of between approximately 1-25 millimeters, preferably between approximately 3-15 millimeters, more preferably between approximately 5-10 millimeters and most preferably approximately 8 millimeters.

The term "hydrolyzed material" as used herein refers to any biological material that has been subjected to high heat and/or enzymatic treatment. Such hydrolyzed materials would be expected to have phospholipid/peptide components that are physically separated from the components of the chitinous exoskeleton.

The term "crustacean" as used herein refers to any marine organism have a hard outside shell (e.g., a chitinous exoskeleton combined with a carbonate) encompassing a fleshy interior that is a living organism. More specifically, the crustaceans are usually considered a large class of mostly aquatic arthropods that have a chitinous or calcareous and chitinous exoskeleton, a pair of often much modified appendages on each segment, and two pairs of antennae. For example, a crustacean may include but not limited to, krill, lobsters, shrimps, crabs, wood lice, water fleas, and/or barnacles.

The term "horizontal centrifuge" refers to any device that is capable of rotating a mixture in the Z-plane (as opposed to the X-plane and/or Y-plane as with conventional centrifuges). This rotation is generated by a screw-type conveyor element aligned horizontally within a tube shaped enclosure. The induced centrifugal force then layers the heavier particles to the outside edges of the enclosure, while the lighter particles form layers closer to the center of the enclosure. Some horizontal centrifuges are modified to comprise an extended separation pathway and induce high gravitational forces (e.g., a sedicanter).

The term "fluoride" as used herein interchangeably and refer to any compound containing an organofluoride and/or an inorganic fluoride.

The term "high fluoride solid fraction" as used herein refers to a composition containing the vast majority of a crustacean's exoskeleton following a low g-force (e.g., between approximately 1,000-1,800 g) horizontal centrifugation separation of a hydrolyzed and disintegrated crustacean material. This fraction contains small particles of exoskeleton of the crustacean that retains the vast majority of fluoride (i.e., for example, between 50-95%) in these organisms.

The term "low fluoride" as used herein may refer to the product of any method and/or process that reduced the fluoride from the original material by approximately 10-fold (i.e., for example, from 5 ppm to 0.5 ppm). For example, 'a low fluoride crustacean phospholipid-protein complex' comprises ten-fold less fluoride than 'a low fluoride hydrolyzed and disintegrated crustacean material'.

The term "low fluoride hydrolyzed material fraction" as used herein refers to a composition containing the vast majority of a crustacean's fleshy internal material following a low g-force (e.g., between approximately 1,000-1,800 g) horizontal centrifugation separation of a hydrolyzed and disintegrated crustacean material. This fraction contains small particles of phospholipids, neutral lipids, proteins and/or peptides that is largely devoid of any fluoride (i.e., for example, between 5%-50% of the raw hydrolyzed and disintegrated material).

The term "a low fluoride phospholipid-peptide complex composition subfraction" as used herein refers to a low fluoride composition containing the vast majority of lipid material following a high g-force (e.g., between approximately 5,000-10,000 g) horizontal centrifugation separation of a low fluoride hydrolyzed material fraction.

The term "concentrated hydrolysate composition subfraction" as used herein refers to a low fluoride composition containing the vast majority of water soluble lean material following a high g-force (e.g., between approximately 5,000-10,000 g) horizontal centrifuge separation of a low fluoride hydrolyzed material fraction.

The term "phospholipid composition" as used herein refers to a low fluoride composition comprising a high percentage of polar lipids (e.g., approximately 75%) created by the extraction of a de-oiled phospholipid-peptide complex using a co-solvent, such as ethanol.

The term "protein hydrolysate" as used herein refers to a low fluoride composition comprising a high percentage of protein (e.g., approximately 70-80%) created by the extraction of a de-oiled phospholipid-peptide complex using a co-solvent, such as ethanol.

The term "immediately" as used herein refers to a minimum practical period between decking a crustacean catch in a trawl bag and/or net coupled with a direct transfer to a suitable disintegrator. For example, this minimum practical period should preferably not exceed 60 minutes, more preferred to not exceed 30 minutes, even more preferred to not exceed 15 minutes.

The term "hydrolysis" as used herein refers to any break and/or disruption made in a protein structure of a disintegrated crustacean material, wherein in the naturally occurring protein sequences become shorter (i.e., for example, by breaking peptide bonds of the amino acid sequence primary structure) and/or denatured (i.e., for example, an unfolding of the amino acid sequence secondary, tertiary and/or quaternary structure). This process may be controlled by hydrolytic enzyme(s). For example, one or more exogenous proteolytic enzymes (e.g. alkalase, neutrase, and enzymes derived from microorganisms or plant species) may be used in the process. Co-factors such as specific ions can be added depending on the used enzymes. The selected enzyme(s) can also be chosen for reducing emulsions caused by high content of phospholipids in the raw material. Besides the temperature, the hydrolysis takes place within optimal or near-optimal pH and sufficient time. For example, the exogenous enzyme alkalase the optimum pH is about 8, optimum temperature about 60° C. and the hydrolysis time 40-120 minutes.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "solvent unit" refers to any enclosed volume configure to heat and pressurize a mixture of supercritical carbon dioxide fluid and/or a co-solvent (e.g., ethanol). Such an enclosed volume may be constructed out of any suitable material including but not limited to metals (e.g., steel, aluminum, iron etc.), plastics (e.g., polycarbonate, polyethylene etc.), fiberglass (etc.).

The term "extraction tank" refers to any enclosed volume configured to withstand heat and pressure sufficient to perform lipid and protein extraction from a raw biomass using a supercritical carbon dioxide fluid. As designed, the extraction tank contemplated herein is configured such that the solvents containing the extracted lipids and proteins rise to the tank top for transfer to a separator unit. Such an enclosed volume may be constructed out of any suitable material including but not limited to metals (e.g., steel, aluminum, iron etc.), plastics (e.g., polycarbonate, polyethylene etc.), fiberglass (etc.).

The term "separator unit" refers to any enclosed volume configured with a centrifuge capable of separating the components of the extracted lipids and proteins received from an extraction tank. The respective extraction components exit the separator unit via outlet ports such that the remaining solvents (i.e., supercritical $CO_2$) are transferred to an absorbent unit for recycling. Such an enclosed volume may be constructed out of any suitable material including but not limited to metals (e.g., steel, aluminum, iron etc.), plastics (e.g., polycarbonate, polyethylene etc.), fiberglass (etc.).

The term "absorbent unit" refers to any enclosed volume configured with materials that will remove contaminants from a supercritical $CO_2$ fluid. Such materials may include, but are not limited to charcoal, coal, purifying gases, plastic polymer resins and/or filtration cartridges comprising single or dual-flat extruded nets (Tenax UK LTD, Wrexham, North Wales LL13 9JT, UK). Such an enclosed volume may be constructed out of any suitable material including but not limited to metals (e.g., steel, aluminum, iron etc.), plastics (e.g., polycarbonate, polyethylene etc.), fiberglass (etc.).

The term "in fluidic communication" refers to any means by which a fluid can be transported from one location to another location. Such means may include, but are not limited to pipes, buckets and/or troughs. Such means may be constructed out of any suitable material including but not limited to metals (e.g., steel, aluminum, iron etc.), plastics (e.g., polycarbonate, polyethylene etc.), fiberglass (etc.).

DETAILED DESCRIPTION OF THE INVENTION

Figure 1:
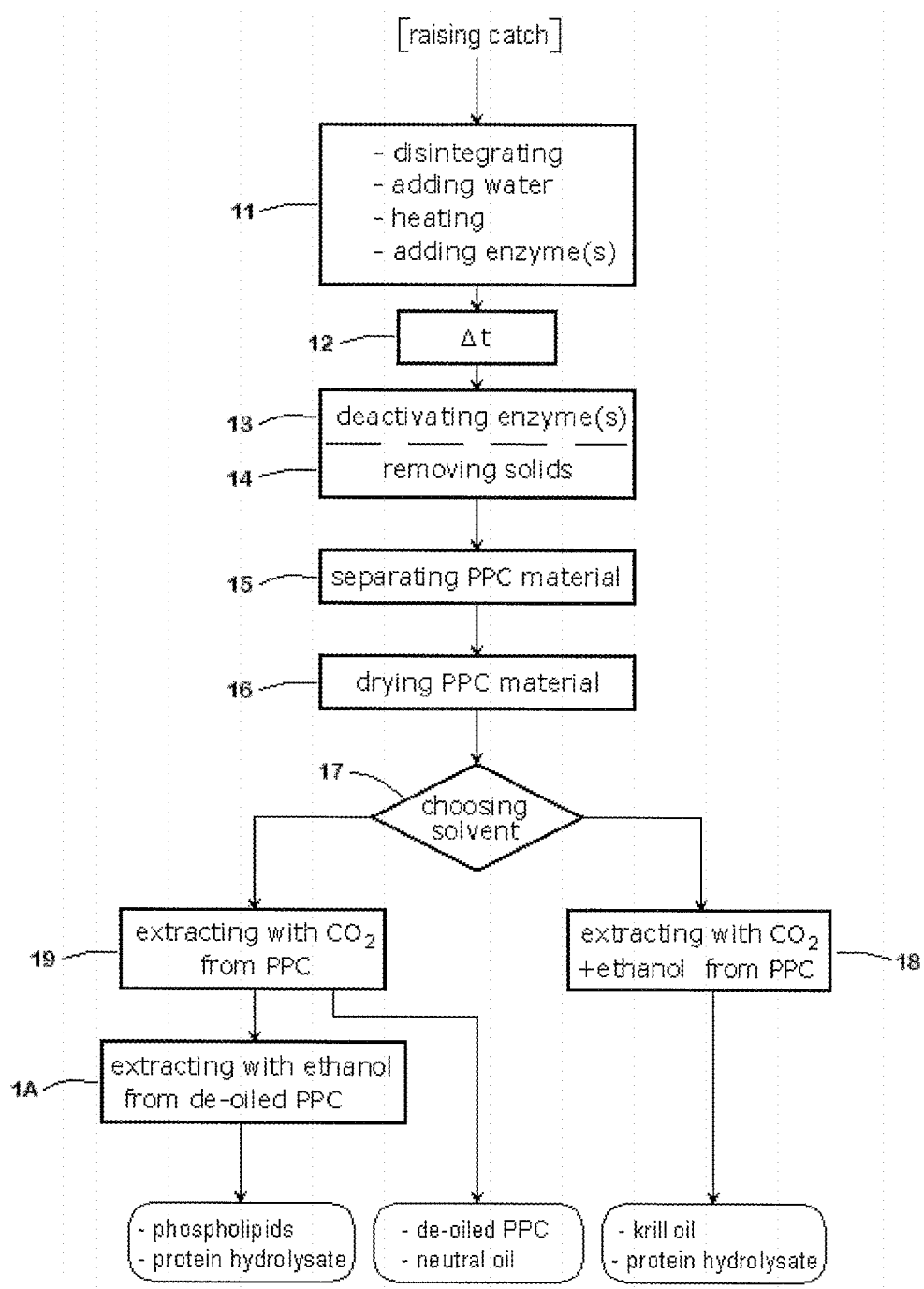
FIG. 1 presents a flow diagram of one embodiment of a method to produce a low fluoride crustacean material.

The present invention is related to the regulation of the cardiovascular system. In particular, to krill powder compositions and their administration to mammal for regulation of blood pressure.

In one embodiment, the present invention comprises the administration of a krill powder composition to slightly obese men and women with moderately elevated blood pressure. In one embodiment, the administration had a duration of at least eight (8) weeks. In one embodiment, the present method compares adverse events between groups of randomised, slightly obese, subjects with moderately elevated blood pressure after ingestion of Antarctic krill powder or after ingestion of a placebo. In one embodiment, the present invention compares systolic and diastolic blood pressure (mean values at the end of trial, and change from baseline) between groups of randomised, slightly obese, subjects with moderately elevated blood pressure after ingestion of Antarctic krill powder or after ingestion of a placebo. In other embodiments, mean values of clinical chemistry and hematology variables including, but not limited to, serum total or lipoprotein lipids are measured. Alternatively, optional samples for analysis of serum lipid fatty acid composition, apolipoproteins, endothelial, inflammatory and hemostatic markers may also be obtained.

I. High Blood Pressure

Blood pressure is a parameter that quantitates the force with which blood pushing against the walls of your arteries. Usually, it is measured in terms of a displacement of mercury (Hg), annotated as a linear displacement (mm Hg). Modern blood pressure devices are electronic, but still display the results in units of mercury displacement.

Blood pressure is highest when your heart beats and is termed a "systolic" pressure. Blood pressure is lowest when your heart is at rest (i.e., between beats) and is termed a "diastolic" pressure. Clinical assessments utilize both the systolic and diastolic numbers where the systolic number comes before or above the diastolic number. For example, a reading of:

119/79 or lower is normal blood pressure
140/90 or higher is high blood pressure Systolic blood pressures ranging between 120-139, or diastolic blood pressures ranging between 80 and 89 are usually sufficient to classify a patient as "prehypertensive". Prehypertension suggest that, without intervention a clinical state of high blood pressure (e.g., hypertension) may result.

High blood pressure usually has no symptoms, but it can cause serious problems such as stroke, heart failure, heart attack and kidney failure. Conventionally, clinical practice has recommended that high blood pressure can be controlled through healthy lifestyle habits such as exercise and the Dietary Approaches to Stop Hypertension (DASH) diet and/or by taking medicines, if needed. DASH is an eating plan that is based on research studies sponsored by the National Heart, Lung, and Blood Institute (NHLBI). These studies showed that DASH lowers high blood pressure and improves levels of cholesterol. This reduces your risk of getting heart disease. The DASH Diet: i) emphasizes vegetables, fruits, and fat-free or low-fat dairy products; ii) includes whole grains, fish, poultry, beans, seeds, nuts, and vegetable oils; and ii) limits sodium, sweets, sugary beverages, and red meats.

Anyone can develop high blood pressure; however, age, race or ethnicity, being overweight, gender, lifestyle habits, and a family history of high blood pressure can increase your risk for developing high blood pressure. Blood pressure tends to rise with age. About 65 percent of Americans age 60 or older have high blood pressure. However, the risk for prehypertension and high blood pressure is increasing for children and teens, possibly due to the rise in the number of overweight children and teens. High blood pressure is more common in African American adults than in Caucasian or Hispanic American adults.

Prehypertension more likely to develop in overweight (e.g., moderately obese) or obese persons. The terms "overweight" and "obese" refer to body weight that's greater than what is considered healthy for a certain height. The most common way to find out whether a subject is overweight or obese is to determine the body mass index (BMI) that is an estimate of body fat. While there are many BMI calculators available, including on the internet, the following table provides some insight into the relationship between height (feet/inches) and weight (pounds) when determining the BMI score of a subject:

| Height | BMI Score | | | | | | | | | | |
|--------|-----|-----|-----|-----|-----|-----|-----|-----|-----|-----|-----|
|        | 21  | 22  | 23  | 24  | 25  | 26  | 27  | 28  | 29  | 30  | 31  |
| 4'10"  | 100 | 105 | 110 | 115 | 119 | 124 | 129 | 134 | 138 | 143 | 148 |
| 5'0"   | 107 | 112 | 118 | 123 | 128 | 133 | 138 | 143 | 148 | 153 | 158 |
| 5'1"   | 111 | 116 | 122 | 127 | 132 | 137 | 143 | 148 | 153 | 158 | 164 |
| 5'3"   | 118 | 124 | 130 | 135 | 141 | 146 | 152 | 158 | 163 | 169 | 175 |
| 5'5"   | 126 | 132 | 138 | 144 | 150 | 156 | 162 | 168 | 174 | 180 | 186 |
| 5'7"   | 134 | 140 | 146 | 153 | 159 | 166 | 172 | 178 | 185 | 191 | 198 |
| 5'9"   | 142 | 149 | 155 | 162 | 169 | 176 | 182 | 189 | 196 | 203 | 209 |
| 5'11"  | 150 | 157 | 165 | 172 | 179 | 186 | 193 | 200 | 208 | 215 | 222 |
| 6'1"   | 159 | 166 | 174 | 182 | 189 | 197 | 204 | 212 | 219 | 227 | 235 |
| 6'3"   | 168 | 176 | 184 | 192 | 200 | 208 | 216 | 224 | 232 | 240 | 248 |

These BMI scores can then be grouped into clinically relevant classifications:

| BMI | Classification |
|-----|----------------|
| 18.5-24.9 | Normal weight |
| 25.0-29.9 | Overweight |
| 30.0-39.9 | Obese |
| 40.0 and above | Extreme obesity |

Although BMI can be used for most men and women, it does have some limits. It may overestimate body fat in athletes and others who have a muscular build. BMI also may underestimate body fat in older people and others who have lost muscle.

II. Conventional Krill Powder Effects on Cardiovascular Regulation

Recently, those in the art have investigated potential cardioprotective activity of protein or peptides derived from marine sources. Although it is not necessary to understand the mechanism of an invention, it is believed that these bioactive marine peptides are latent within a parent marine protein sequence and only become bioactive when released by proteolytic digestion during gastrointestinal digestion or via food processing. Nonetheless, human data on antihypertensive activity of krill-derived protein hydrolysates/peptides is lacking and non-enabling. (Hardeny & Fitzgerald 2013, Lee et al. 2012, Martinez-Maqueda et al 2012). In one embodiment, the present invention contemplates that krill powders comprising approximately 55% protein may have clinical effects on blood pressure as well as other vascular elasticity markers.

Elevated blood pressure or hypertension is a risk factors for cardiovascular diseases. Although the etiology of high blood pressure is believe to comprise a genetic component, many lifestyle factors including, but not limited to dietary factors, have been suggested to contribute to it (ESH and ESC Guidelines 2013). For example, since reduction of salt has not resulted in widespread clinical efficacy to reduce blood pressure, additional dietary interventions and measures should be investigated.

Long-chain n-3 fatty acids may affect (via multiple mechanisms) a variety of cardiovascular risk factors. Although it is not necessary to understand the mechanism of an invention, it is believed that two of these long-chain n-3 fatty acids (e.g., EPA and DHA) affect cardiovascular risk factors by incorporation into cell membranes. The n-3 polyunsaturated fatty acids (PUFAs) EPA and DHA, which are found in fish oils, may suppress the production of arachidonic-acid-derived eicosanoids and EPA is a substrate for the synthesis of an alternative family of eicosanoids. Thus, dietary fats which are rich in n-3 PUFAs have a potential to alter cytokine production and thus modulate inflammation. Effects of fish oil consumption on circulation levels of inflammatory markers have been studied in healthy and populations with auto-immune disease, and found a significant lowering effect on CRP, TNf-$\alpha$ and IL-6 in most of the studies. (Calder 1997, Calder 2002, Li et al 2014). In addition, EPA and DHA from fish oil are essential fatty acids used for reducing the risk of CVD via modulating hemostatic and inflammatory markers as well. EPA and DHA are known to affect on hemostasis via their inhibitory effects on platelet function, but seem not affect bleeding as such. These fatty acids have been shown to affect via multiple signaling pathways and thrombotic processes beyond simply affecting platelet aggregation. (Wachira et al 2014).

On the other hand, the effect of long-chain n-3 fatty acid on serum LDL cholesterol has been slightly controversial, since it is uncertain as to whether this effect could have been neutral or even adverse with some formulations and in certain patient groups. In general, treatment with EPA+DHA appears to lower patient triglycerides, but in those patients with very high triglyceride levels, use of EPA+DHA may also raise low-density lipoprotein cholesterol levels, whereas EPA alone may not raise LDL levels (Harris 2013). In comparison, krill oils containing dominantly EPA as a long-chain n-3 fatty acid have been shown to be more effective than either EPA+DHA or EPA alone in lowering serum triglycerides and has a neutral effect on LDL cholesterol or has even been reported to lower LDL cholesterol (Krill oil monograph 2010, Bunea et al 2012, Berge et al 2014). High serum triglyceride levels are considered as a risk factor for cardiovascular disease similar to high LDL cholesterol. However, an independent role of triglycerides as an etiologic agent of cardiovascular disease has been debated since it is heavily associated with other risk factors linked to metabolic syndrome like insulin (Andersson et al 2014, Oh et al 2014). The effect of krill or krill oil on other metabolic markers like blood glucose is also controversial as studies have only been made with krill oil (Bunea et al 2012, Trepanowski et al 2012, Sadzuka et al 2012).

Astaxanthin is believed to be a carotenoid that may provide krill powder its reddish colour and may impart anti-oxidative and/or anti-inflammatory properties. As a carotenoid of marine origin, astaxanthin has demonstrated to be very potent antioxidant at protecting membranous phospholipids and other lipids against peroxidation using various models of cardiovascular disease (CVD). Astaxanthin is also believed to be a potential scavenger of free radicals and reactive oxygen and nitrogen species. Oxidative stress and inflammation play an important role in the pathophysiology of many chronic diseases including, but not limited to, CVD. So far, human data collected subsequent to administration of krill-derived has shown little to no effect of astaxanthin on CVD (Guerin et al 2003, Ciccione et al 2013).

In summary, krill powder with its various bioactive components has been reported to have the potential of improving lipid profile, suppressing lipid peroxidation, and reinforcing the activity of the antioxidant system and thus contrast vascular wall inflammation, stabilize membrane properties or increase vascular elasticity. These effects could prevent progression of atherosclerosis, and finally reduce the risk of CVD, provided that the krill powder can be safely administered without significant adverse effects.

III. Clinically Safe and Tolerable Krill Powder Compositions

In one embodiment, the present invention contemplates a safe and tolerable krill powder derived from Antarctic krill (e.g., Rimfrost Pristine) in slightly obese subject with mildly or moderately elevated blood pressure. In one embodiment, cardiovascular risk factors including, but not limited to, blood pressure, serum lipo-protein lipids and/or apolipoproteins are measured.

A. Verification Protocol

The data presented herein compares the total amount and type of adverse events during an 8-week follow-up after ingestion of a krill powder composition (e.g., Rimfrost Pristine) to a respective amount of placebo ingestion in slightly obese study subjects with mildly or moderately elevated blood pressure. The data also provides monitoring of clinical safety parameters including, but not limited to, blood count, creatinine, gamma glutamyl transferase, blood glucose, ASAT, ALAT and thyrotropin (mean, median). The data also provides monitoring of systolic and diastolic blood pressure. The data also provides monitoring of blood total and lipoprotein lipid analysis. The data also provides monitoring of serum fatty acid concentrations in triglyceride and phospholipid fractions including, but not limited to, blood apolipoprotein concentrations, blood inflammatory markers and/or blood hemostatic markers.

The study design may include, but is not limited to, endpoints such as:
  i) total number and type of reported adverse events (AE) such as those coded by MedDRA and reported with system organ class (SOC) and preferred term (PT) levels, annotated with level of seriousness, level of severity, onset/duration and/or causality.

An adverse event comprises any unfavorable and unintended sign, symptom or medical complaint and worsening of a pre-existing condition. Study subjects kept a diary for the whole duration of the study and were requested to write down all unfavorable symptoms and medical complaints not existing at baseline or significantly worsened from baseline situation. Completeness of the diaries were checked at each study visit. All reported adverse events were recorded, coded and analyzed carefully, in order to determine severity, possible relation to study products, onset and outcome of the adverse event. As a primary endpoint of this study, the total number of reported adverse events were compared in the study subjects groups taking 4-6 capsules (4 g) krill powder or 4-6 capsules (4 g) of placebo for the 8-week follow-up period of the study.
  ii) mean and mean change over the study period in systolic and diastolic blood pressure recorded with 1 mmHg accuracy;
  iii) blood safety parameters including, but not limited to, mean and median variables of blood count, TSH, creatinine, gamma glutamyl transferase, blood glucose, ASAT, ALAT and thyrotropin;

vi) mean concentration of serum total triglycerides, total cholesterol, LDL and HDL-cholesterol;
vii) mean change over the study period in serum total and lipoprotein lipids;
viii) percentages of: a) polyunsaturated (EPA and DHA), b) monounsaturated and saturated fatty acids of total fatty acids in TG and PL lipid fractions and c) omega-3 index;
ix) concentration of blood apolipoprotein (i.e ApoA1, apoB and Ip(a));
x) concentration of blood inflammatory markers (CRP, TNFα, IL-6, ICAM-1, VCAM-1); and/or
xi) concentration of hemostatic markers (i.e. fibrinogen and PAI-1).

The data presented herein was based upon a prospective, randomised, double-blinded, placebo-controlled, single-center intervention study with slightly obese subjects who have mildly or moderately elevated blood pressure. A parallel two-arm design was followed. For each gender, subjects were randomized according to a randomization list into two study groups (krill powder or placebo) in a balanced manner (1:1). The study design comprised the following phases:

i) Pre-Screening Visit

Pre-screening visits were performed by a study nurse to check body mass index (BMI: body weight (kg)/(height (m))$^2$) and blood pressure (mm Hg). Before these measurements study subjects were requested to sign pre-screening visit informed consent form.

Body weight was measured over the study period with the same calibrated, digital scale at each visit while the subjects were wearing light indoor clothing and no shoes and recorded with 0.1 kg precision. The weight measurements were repeated once and the mean of two measurements was used in statistical analysis.

Height was measured with the subject standing straight, hands beside, shoulders relaxed and heels together. The head of the subject should be in so called Frankfurt position; where the auditory canal is horizontally on the same level with the top of lower eyelid. Body height was measured with wall-attached rod to the nearest crossed half a centimeter.

Blood pressure (BP) was measured at all visits using an automatic blood pressure measuring device that had been validated according to standardized protocols and calibrated periodically. Cuff and bladder dimensions of the device should be adapted to the patients' arm circumference. Before BP measurements were taken, study subjects were instructed to avoid heavy physical exercise, smoking and consumption of caffeine rich drinks. BP measurements were conducted in a quiet room where there were no disturbances. Study subjects were seated comfortably, with back supported, legs un-crossed, upper arm bared and subjects are allowed to rest 3-5 minutes cuff assembled, before starting the BP measurement. Discussion before and during the measurement was avoided. Blood pressure was measured from the upper arm, which is supported in the hearth level. Proper size cuff was placed to the upper arm so that middle part of the bladder is on the brachial vein. An appropriate bladder was selected according to study subjects upper arm circumference (e.g. small, standard or large bladder). Three BP measurements spaced 1-2 min apart were taken and recorded with 1 mmHg accuracy. In cases where the first two measures differed significantly (over 10 mmHg), additional measurements were taken. Average of last two measurements were used in the data analysis. At the Pre-Screening Visit, BP measurements were taken repeatedly from both arms and if the measures differed significantly, in the follow-up measurements the arm giving higher values was used.

A lifestyle questionnaire comprising questions related to topics including, but not limited to, smoking, alcohol consumption, physical activity, medication, fish consumption and food supplement use was given by a study nurse in combination with an interview. A structured interview on demographics (e.g., age, sex, ethnicity), previous and current diseases, current medication, alcohol and tobacco consumption and use of dietary supplements (especially fish oil and other n-3 FA supplements, plant sterols and cholesterol lowering fiber supplements (e.g., guar gum, glucomannan, oat fibre etc) and use of fish foods were carried out. A lifestyle questionnaire was replicated at the Day 56 Visit (infra). In addition, study subjects were asked to evaluate the usability of the krill oil powder. Subjects were advised to keep their medication, lifestyle, background diet and body weight constant during the study.

Those subjects fulfilling the inclusion criteria (infra) were scheduled a time for a screening visit and they received informed consent form for the study and patient information package. At the end of pre-screening visit, a medication card was given for the study subjects to be filled in at home in preparation for the subsequent screening visit.

ii) Screening Visit (Study Day −14 to Study Day −7)

During the screening visit inclusion and exclusion criteria were checked for each study subject in order to verify the eligibility. Medical history, concomitant medication and lifestyle variables were evaluated and recorded on a case report form (CRF). Anthropometric, safety screening lab measurements, blood pressure and fasting blood lipoprotein lipid measurements were taken. Instructions for a background diet for the duration of the study were given to study subjects orally and in written (as part of diary) by the study nurse.

Safety screening lab measurements are routine clinical chemistry and hematology measurements including, but not limited to, blood count, serum thyrotropin, serum creatinine, plasma gamma-glutamyl transferase, blood glucose, ASAT, and/or ALAT that are determined after a 10-12 h overnight fasting.

iii) Randomization Visit (Study Day 0)

Randomization of the study subjects into two groups was carried out at Day 0 visit and inclusion and exclusion criteria were verified. When subjects are found eligible to the study, they were randomized according to a randomization list to two study groups (krill powder or placebo) in a balanced manner (1:1), separately for both gender. Permuted block randomization was applied and a concealed allocation method was used. Used block size was reported in the randomization program code.

At Day 0, baseline primary, secondary and optional endpoints were established. These endpoints included, but were not limited to, number of adverse events, safety screening labs, blood pressure, blood lipoprotein lipid analysis, serum fatty acids in PL and TG fraction, apolipoproteins, endothelial, inflammatory and hemostatic markers) measurements. Also, concomitant medication and study subjects' adherence to the proper background diet was checked.

To determine fatty acid composition of TG and PL fraction and an omega-3 index, blood samples were collected into EDTA tubes at fasting at Day 0 and Day 56 follow-up visits. Blood samples for determination of fatty acid composition in plasma PL and TG were directly centrifuged (2000 g, 10 min, 10° C.) and plasma taken off and frozen at −75° C. Buffy coat was taken off, and discarded.

Blood samples were stored at −75° C. before analyzing. All samples collected during the study of one subjects were analyzed within the same batch to exclude batch to batch variation.

Lipids were extracted and TG and PLs were purified by use of Sep-Pak C-18 mini cartridge (Waters, Eschborn, Germany). FA methyl esters were formed by acid hydrolysis, and analyzed by capillary gas-liquid chromatography on a GS2010 Gas Chromatograph (Shimadzu, Duisburg, Germany) equipped with a SP2560, 100-m column (Supelco, Bellefonte, Pa.) using hydrogen as carrier gas. Fatty acids were identified by comparison with a FA standard mixture. Results were expressed as % of total FA in plasma PL.

To determine serum apolipoprotein i.e. apoA1, apoB and lp(A), concentrations blood samples was collected at fasting at Day 0 and Day 56 follow-up visits. Blood samples were mixed well and allowed to clot at least 30 minutes before centrifugation (2000 g, 10 min, 10° C.). Serum was collected and frozen at −20° C.

Optional markers for circulating inflammatory markers (CRP, TNFα, IL-6, ICAM-1, VCAM-1) and for hemostatic markers (fibrinogen and PAI-1) may be obtained on any subject Visit throughout the study period. Blood samples to determine these hemostatic variables should avoid contamination with samples containing tissue thromboplastin or heparin. Venipuncture must be performed with no trauma. The plasma for hemostatic variables were separated and stored at −70° C. until measurement. Blood samples for ICAM-1 and VCAM-1 analysis were collected to pre-cooled EDTA tubes on ice. Samples were centrifuged (2400 g, 10 min, +4 C) and plasma taken off and frozen at −70° C. Other blood samples for optional analysis were stored at −20° C. before analyzing. All samples collected during the study of one subjects were analyzed in the same batch to exclude batch to batch variation.

iv) Data Collection Visits (Study Day 14, Study Day 28 and Study Day 56)

An 8-week safety and tolerance data collection period in combination with the Pre-Screening and Screening Visits provided a total study duration of approximately 10 weeks. Optionally a Screening Visit may be extended up to 4 weeks before the initiation of the study if there is a need for wash-out from previous consumption of n-3 fatty acid preparations.

On the Study Day 14 Visit, concomitant medication administration and compliance to krill powder ingestion was checked as recorded in the subject diaries. All adverse events reported by the subjects in their study diaries since the Randomization Visit were recorded and blood pressure was measured.

On the Study Day 28 Visit, body weight, concomitant medication administration, compliance to krill powder ingestion, and background diet were checked. All adverse events reported by the subjects in their study diaries since the Study Day 14 Visit were collected and blood pressure measurements were taken. During the Study Day 28 Visit safety laboratory measurements and blood lipoprotein measurements were taken.

On the Study Day 56 Visit, all primary, secondary and optional endpoint measurements were performed. All adverse events reported by the subjects in their study diaries since the Day 28 Visit were checked and collected. In addition, a krill powder accountability assessment was performed to verify appropriate compliance during the study period (e.g, at least 80%). Also, study subject's weight at the end of the study was determined, in addition to recording concomitant medication administration and overall adherence to the background diet.

Study subjects were instructed to follow normal fasting procedures before the study visits if blood samples are taken, i.e. to be without food and drink (except small amount of water) 10-12 h before sampling and to avoid alcohol consumption also the day before laboratory tests. Subjects were not allowed to drink coffee or any other caffeine containing drinks/foods before blood pressure measurements are completed. Between the data collection visits a study subject can follow their habitual diet, except the consumption of fish oil capsules and other food supplements that can have effect on blood pressure and blood lipid values were not allowed. To be eligible for inclusion, the subject fulfilled all of the following criteria:
1. Age 18-65 years
2. Slightly obese female and male subjects (BMI between 25-30 kg/m2)
3. Mildly or moderately elevated blood pressure (RR systolic 140-159/diastolic 90-99)
4. Signed written informed consent On the other hand, the presence of any of the following criteria excluded a subject from participating in the study:
1. Medication potential to affect on serum lipids (lipid-lowering drugs)
2. Familial hypercholesterolemia, marked combined hyperlipidemia, condition that would impair fat absorption (e.g. chronic pancreatitis, pancreatic lipase deficiency syndrome)
3. Any untreated medical condition affecting absorption of fat
4. Type 1 and 2 diabetes
5. Cancer or other malignant disease within the past five years
6. Periodical hormone replacement therapy
7. High intake of oily fish (>2 times per week as a principal meal) (i.e. salmon, herring, sardines, mackerel, vendace)
8. Smoking
9. Alcohol consumption>15 doses per week
10. Pregnant, lactating or wish to become pregnant
11. Hypersensitivity to fish or any of the components of the test products
12. Regular use of n-3 or other fatty acid supplements, plant sterols or fiber supplements 4 weeks before randomization
13. Lack of suitability for participation in the trial, for any medical reason, as judged by the Principal Investigator.

Subjects were withdrawn from the study if pregnancy or any other diagnosed medical condition or treatment stated above as the exclusion criteria took place during the study. Subjects withdrawn for any reason once they had started the first intervention day were not replaced. All study subjects had a right to discontinue at any point, if he or she wants to stop taking part in the study. Subjects having compliance less than 80% of planned dose were excluded from data analysis.

A study and measurement schedule summary is shown where +/−3 days are allowed as deviation for each visit. See, Table 1.

TABLE 1

| | Summary Of Study Protocol | | | | | |
|---|---|---|---|---|---|---|
| | Visit number: | | | | | |
| Type of action: | Visit 1 Pre-Screening | Visit 2 Screening Day −7-(−14) | Visit 3 Baseline Day 0 | Visit 4 Day 14 ± 3 | Visit 5 Day 28 ± 3 | Visit 6 End Day 56 ± 3 |
| Screening measurements | | | | | | |
| Written consent | | x | x | | | |
| Incl./Excl. criteria | | x | x check | | | |
| Anthropometric measurements (weight, height, body mass index) | x | x | x weight only | | x weight only | x weight only |
| Medical history | | x | | | | |
| Concomitant medication | | x | x | x | x | x |
| Lifestyle questionnaire (smoking, alcohol, physical activity, fish consumption and food supplement use) | | x | | | | x |
| Instructions/follow-up on background diet (fish and n-3 fa limitations) | | x | x | | x | x |
| Randomization | | | x | | | |
| IP dispensation | | | x | x | x | |
| Efficacy variables | | | | | | |
| Adverse events (subject diaries) | | x | x | x | x | x |
| Blood pressure measurement | x | x | x | x | x | x |
| Safety lab (blood count, TSH, creatinine, gamma glutamyl transferase, blood glucose, ASAT, ALAT) | | x | x | | x | x |
| Blood samples for total triglycerides, total cholesterol, LDL and HDL-cholesterol levels | | | x | | x | x |
| Optional samples | | | | | | |
| Blood samples for serum fatty acid composition of lipids in PL and TG fraction and omega-3 index | | | x | | | x |
| Blood samples for apoB, apoA1 and Ip(a) | | | x | | | x |
| Blood sample for circulating inflammatory markers (CRP and optional markers: TNFα, IL-6, ICAM-1, VCAM-1) | | | x | | | x |
| Blood sample for hemostatic markers (fibrinogen and PAI-1) | | | x | | | x |

The krill powder capsule administered in the experimental group of this study is an Antarctic krill powder (*Euphausia Superba*), commercialized as Rimfrost Pristine™. The control group in the study was administered an inert placebo capsule. The krill powder capsule and placebo capsule were made from the same Maize starch or respective material. See, Table 2. Further, any added excipients and/or masking flavour were used in both the krill powder and placebo capsules. The capsules were taken orally.

TABLE 2

| Krill Powder And Placebo Capsule Characteristics | | | |
|---|---|---|---|
| Trade name | Product name | Composition | Storage |
| Rimfrost Pristine ™ | Antarctic Krill powder from | Reddish powder from Antarctic Krill (*Euphausia superba*) rich in marine omega-3 phospholipids, proteins, peptides and astaxanthin | store dark in the fridge at 2-8° C. |
| NA | Placebo | capsule with maize starch | store dark in the fridge at 2-8° C. |

The krill powder doses administered in this study are presented in Table 3.

TABLE 3

Doses of krill powder and placebo capsules

| Test Product | Dose | Total fat | Total protein | Total omega-3 (expressed as FFA) | EPA | DHA | Esterified astaxanthin |
|---|---|---|---|---|---|---|---|
| Krill powder | 4 g | 360 mg | max 2.2 g | 200 mg | 100 mg | 60 mg | 0.16 mg |
| Placebo | 4 g | 0 g | max 2.2 g | 0 g | 0 g | 0 g | 0 g |

B. Adverse Event Results

The data demonstrates that krill powder administration reduced both the frequency of adverse events as well as the number of affected subjects when compared to placebo. Table 4.

TABLE 4

Summary of Adverse Events: Frequency of ICD-10 Class Events (F); Number Of Affected Subjects (AP) and Percentage of Patients Affected By Adverse Events (%: underlined)

| | Product | | | | | | | | |
|---|---|---|---|---|---|---|---|---|---|
| | All (N = 35) | | | Krill Powder (N = 18) | | | Placebo (N = 17) | | |
| Classified Event | F | AP | % | F | AP | % | F | AP | % |
| Total | 80 | 26 | 74.3 | 30 | 10 | 55.6 | 50 | 16 | 94.1 |
| Gastrointestinal | 23 | 13 | 37.1 | 11 | 5 | 27.8 | 12 | 8 | 47.1 |
| Mental, behavioral | 2 | 2 | 5.7 | . | . | . | 2 | 2 | 11.8 |
| Musculoskeletal[i] | 15 | 9 | 25.7 | 4 | 3 | 16.7 | 11 | 6 | 35.3 |
| Nervous system[ii] | 14 | 7 | 20.0 | 8 | 3 | 16.7 | 6 | 4 | 23.5 |
| Other[iii] | 6 | 5 | 14.3 | . | . | . | 6 | 5 | 29.4 |
| Respiratory[iv] | 20 | 15 | 42.9 | 7 | 5 | 27.8 | 13 | 10 | 58.8 |

[i]including injuries;
[ii]including headaches;
[iii]including unclassified abnormal laboratory values;
[iv]including common colds A Rate ratio (krill powder/placebo) of adverse events counts was calculated using a poisson regression model:

| Contrast Estimate Results | | | |
|---|---|---|---|
| Label | Mean Estimate | Mean Confidence | Limits |
| trt rate ratio | 0.5667 | 0.3604 | 0.8911 |

In general, gastrointestinal, musculoskeletal, and respiratory adverse events were approximately 50% lower in the Krill Powder group as compared to the Placebo group (compare underlined percentage (%) columns between each group).

C. Low Density Lipoprotein Level Results

Low Density Lipoprotein levels were seen not to be appreciably altered when comparing the Krill Powder group to the Placebo group over the duration of the study period. See, Table 5.

TABLE 5

Low Density Lipoprotein Levels Over The Study Period (UNITS??)

| Treatment | VISIT | N | MEAN | SD | SE | MIN | Q1 | MEDIAN | Q3 | MAX |
|---|---|---|---|---|---|---|---|---|---|---|
| All | BAS | 35 | 3.92 | 0.92 | 0.16 | 1.9 | 3.1 | 4.1 | 4.5 | 6.0 |
| | D28 | 35 | 3.83 | 0.85 | 0.14 | 2.4 | 3.2 | 3.7 | 4.3 | 5.7 |
| | D56 | 35 | 3.90 | 0.86 | 0.14 | 2.4 | 3.2 | 3.9 | 4.5 | 5.8 |
| Krill Powder | BAS | 18 | 3.98 | 0.94 | 0.22 | 1.9 | 3.3 | 4.2 | 4.8 | 5.6 |
| | D28 | 18 | 3.87 | 0.91 | 0.21 | 2.4 | 3.2 | 3.6 | 4.5 | 5.7 |
| | D56 | 18 | 3.95 | 0.88 | 0.21 | 2.4 | 3.4 | 3.8 | 4.5 | 5.8 |
| Placebo | BAS | 17 | 3.86 | 0.93 | 0.22 | 2.8 | 3.1 | 3.7 | 4.3 | 6.0 |
| | D28 | 17 | 3.79 | 0.81 | 0.20 | 2.4 | 3.1 | 3.7 | 4.3 | 5.4 |
| | D56 | 17 | 3.85 | 0.86 | 0.21 | 2.7 | 3.2 | 3.9 | 4.5 | 5.6 |

BAS = baseline at Study Day 0.
D28 = Study Day 28
D56 = Study Day 56

When each group at Study Day 28 was compared to its respective baseline, each group reflected mean differences in LDL levels of approximately 1% or less which was well within the Standard Error of the Mean range. See, Table 6.

TABLE 6

Percentage Change Of LDL levels at Study Day 28 compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | −0.8 | 13.6 | 2.3 | −43 | −7 | 0 | 5 | 29 |
| Krill Powder | D28 | 18 | −0.6 | 17.4 | 4.1 | −43 | −6 | 0 | 14 | 29 |
| Placebo | D28 | 17 | −1.1 | 8.5 | 2.1 | −14 | −7 | 0 | 5 | 19 |

A similar evaluation of the differences in the raw data measurements provided in Table 5, show that the changes in mean LDL levels did not fluctuate more than approximately 0.1 X/X that were within the Standard Error of the Mean range. See, Table 7.

TABLE 7

Raw Value Change of LDL levels at Study Day 28 compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | −0.09 | 0.62 | 0.11 | −2.4 | −0.3 | 0.0 | 0.2 | 1.2 |
| Krill Powder | D28 | 18 | −0.11 | 0.82 | 0.19 | −2.4 | −0.3 | 0.0 | 0.4 | 1.2 |
| Placebo | D28 | 17 | −0.07 | 0.33 | 0.08 | −0.6 | −0.2 | 0.0 | 0.2 | 0.6 |

When each group at Study Day 56 was compared to its respective baseline, each group reflected mean differences in LDL levels of approximately 1% or less which was well within the Standard Error of the Mean range. See, Table 8.

TABLE 8

Percentage Change Of LDL levels at Study Day 56 compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 1.0 | 15.4 | 2.6 | −28 | −7 | 0 | 7 | 39 |
| Krill Powder | D56 | 18 | 1.2 | 16.8 | 4.0 | −28 | −11 | 3 | 11 | 32 |
| Placebo | D56 | 17 | 0.7 | 14.3 | 3.5 | −25 | −6 | 0 | 4 | 39 |

A similar evaluation of the differences in the raw data measurements provided in Table 5, show that the changes in mean LDL levels did not fluctuate more than approximately 0.03 X/X that were within the Standard Error of the Mean range. See, Table 9.

TABLE 9

Raw Value Change of LDL levels at Study Day 56 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | −0.02 | 0.59 | 0.10 | −1.4 | −0.3 | 0.0 | 0.3 | 1.2 |
| Krill Powder | D56 | 18 | −0.03 | 0.66 | 0.16 | −1.4 | −0.3 | 0.1 | 0.4 | 1.1 |
| Placebo | D56 | 17 | −0.01 | 0.52 | 0.13 | −1.0 | −0.2 | 0.0 | 0.1 | 1.2 |

D. High Density Lipoprotein Results

High Density Lipoprotein levels were seen not to be appreciably altered when comparing the Krill Powder group to the Placebo group over the duration of the study period. See, Table 10.

TABLE 10

High Density Lipoprotein Levels Over the Study Period

| Treatment | VISIT | N | MEAN | SD | SE | MIN | Q1 | MEDIAN | Q3 | MAX |
|---|---|---|---|---|---|---|---|---|---|---|
| All | BAS | 35 | 1.56 | 0.48 | 0.08 | 0.8 | 1.2 | 1.5 | 1.8 | 3.0 |
| | D28 | 35 | 1.56 | 0.44 | 0.07 | 0.8 | 1.3 | 1.5 | 1.7 | 2.8 |
| | D56 | 35 | 1.60 | 0.48 | 0.08 | 0.8 | 1.2 | 1.6 | 1.9 | 2.7 |
| Krill Powder | BAS | 18 | 1.49 | 0.58 | 0.14 | 0.8 | 1.1 | 1.4 | 1.8 | 3.0 |
| | D28 | 18 | 1.46 | 0.47 | 0.11 | 0.8 | 1.2 | 1.4 | 1.6 | 2.8 |
| | D56 | 18 | 1.48 | 0.50 | 0.12 | 0.8 | 1.1 | 1.5 | 1.7 | 2.6 |
| Placebo | BAS | 17 | 1.63 | 0.34 | 0.08 | 1.1 | 1.4 | 1.5 | 1.8 | 2.4 |
| | D28 | 17 | 1.67 | 0.38 | 0.09 | 1.2 | 1.5 | 1.6 | 1.7 | 2.6 |
| | D56 | 17 | 1.72 | 0.43 | 0.10 | 1.2 | 1.4 | 1.6 | 1.9 | 2.7 |

BAS = Baseline at Study Day 0;
D28 = Study Day 28;
D56 = Study Day 56

When each group at Study Day 28 was compared to its respective baseline, each group reflected mean differences of HDL that were approximately 2.5% or less which was well within the Standard Error of the Mean range. See, Table 11.

TABLE 11

Percentage Change Of HDL levels at Study Day 28 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | 1.7 | 9.2 | 1.6 | −19 | −5 | 3 | 7 | 30 |
| Krill Powder | D28 | 18 | 0.9 | 10.8 | 2.5 | −19 | −7 | 2 | 7 | 30 |
| Placebo | D28 | 17 | 2.5 | 7.5 | 1.8 | −10 | −3 | 4 | 6 | 17 |

A similar evaluation of the differences in the raw data measurements provided in Table 10, show that the changes in mean HDL levels did not fluctuate more than approximately 0.04 X/X that were within the Standard Error of the Mean range. See, Table 12.

TABLE 12

Raw Value Change of HDL levels at Study Day 28 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | 0.01 | 0.15 | 0.03 | −0.5 | −0.1 | 0.1 | 0.1 | 0.3 |
| Krill Powder | D28 | 18 | −0.03 | 0.16 | 0.04 | −0.5 | −0.1 | 0.0 | 0.1 | 0.2 |
| Placebo | D28 | 17 | 0.04 | 0.12 | 0.03 | −0.2 | −0.1 | 0.1 | 0.1 | 0.3 |

When each group at Study Day 56 was compared to its respective baseline, each group reflected mean differences of HDL that were approximately 5% or less, where the fluctuation of the Krill Powder group was less than the Placebo group. See, Table 13.

TABLE 13

Percentage Change Of HDL levels at Study Day 56 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 3.2 | 10.8 | 1.8 | −15 | −5 | 3 | 9 | 27 |
| Krill Powder | D56 | 18 | 1.4 | 11.6 | 2.7 | −15 | −6 | −0 | 8 | 25 |
| Placebo | D56 | 17 | 5.2 | 9.9 | 2.4 | −8 | −3 | 4 | 9 | 27 |

A similar evaluation of the differences in the raw data measurements provided in Table 10, show that the changes in mean HDL levels did not fluctuate more than approximately 0.09 X/X where the fluctuation of the Krill Powder group was less than the Placebo group. See, Table 14.

TABLE 14

Raw Value Change of HDL levels at Study Day 56 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 0.04 | 0.18 | 0.03 | −0.4 | −0.1 | 0.0 | 0.1 | 0.5 |
| Krill Powder | D56 | 18 | −0.01 | 0.17 | 0.04 | −0.4 | −0.1 | −0.0 | 0.1 | 0.3 |
| Placebo | D56 | 17 | 0.09 | 0.18 | 0.04 | −0.1 | −0.0 | 0.1 | 0.2 | 0.5 |

E. Total Cholesterol Results

Total cholesterol levels were seen not to be appreciably altered when comparing the Krill Powder group to the Placebo group over the duration of the study period. See, Table 15.

TABLE 15

Total Cholesterol Levels Over the Study Period

| Treatment | VISIT | N | MEAN | SD | SE | MIN | Q1 | MEDIAN | Q3 | MAX |
|---|---|---|---|---|---|---|---|---|---|---|
| All | BAS | 35 | 5.79 | 0.89 | 0.15 | 4.2 | 5.2 | 5.7 | 6.3 | 8.4 |
|  | D28 | 35 | 5.68 | 0.87 | 0.15 | 4.3 | 5.1 | 5.7 | 6.0 | 7.7 |
|  | D56 | 35 | 5.79 | 0.89 | 0.15 | 3.9 | 5.1 | 5.8 | 6.3 | 8.2 |
| Krill Powder | BAS | 18 | 5.78 | 0.80 | 0.19 | 4.2 | 5.2 | 5.6 | 6.4 | 7.3 |
|  | D28 | 18 | 5.66 | 0.91 | 0.21 | 4.3 | 5.1 | 5.6 | 6.3 | 7.7 |
|  | D56 | 18 | 5.76 | 0.87 | 0.20 | 3.9 | 5.2 | 5.7 | 6.1 | 7.5 |
| Placebo | BAS | 17 | 5.79 | 1.00 | 0.24 | 4.4 | 5.1 | 5.7 | 6.2 | 8.4 |
|  | D28 | 17 | 5.71 | 0.86 | 0.21 | 4.4 | 5.2 | 5.8 | 6.0 | 7.6 |
|  | D56 | 17 | 5.84 | 0.94 | 0.23 | 4.6 | 5.1 | 5.9 | 6.3 | 8.2 |

BAS = Baseline at Study Day 0;

D28 = Study Day 28;

D56 = Study Day 56

When each group at Study Day 28 was compared to its respective baseline, each group reflected mean differences of total cholesterol that were approximately 1.7% or less that were within the Standard Error of the Mean range. See, Table 16.

TABLE 16

Percentage Change Of Total Cholesterol levels at Study Day 28 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | −1.4 | 9.9 | 1.7 | −30 | −6 | −2 | 4 | 21 |
| Krill Powder | D28 | 18 | −1.7 | 12.5 | 3.0 | −30 | −7 | −2 | 4 | 21 |
| Placebo | D28 | 17 | −1.0 | 6.5 | 1.6 | −12 | −5 | −2 | 2 | 13 |

A similar evaluation of the differences in the raw data measurements provided in Table 15, show that the changes in mean total cholesterol levels did not fluctuate more than approximately 0.13 X/X that were within the Standard Error of the Mean range. See, Table 17.

TABLE 17

Raw Value Change of Total Cholesterol levels at Study Day 28 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | −0.11 | 0.63 | 0.11 | −2.2 | −0.4 | −0.1 | 0.2 | 1.2 |
| Krill powder | D28 | 18 | −0.13 | 0.81 | 0.19 | −2.2 | −0.4 | −0.1 | 0.2 | 1.2 |
| Placebo | D28 | 17 | −0.08 | 0.38 | 0.09 | −0.8 | −0.3 | −0.1 | 0.1 | 0.7 |

When each group at Study Day 56 was compared to its respective baseline, each group reflected mean differences of total cholesterol that were approximately 1.3% or less that were within the Standard Error of the Mean range. See, Table 18.

TABLE 18

Percentage Change Of Total Cholesterol levels at Study Day 56 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 0.5 | 9.2 | 1.6 | −20 | −4 | 0 | 6 | 19 |
| Krill powder | D56 | 18 | −0.2 | 9.6 | 2.3 | −17 | −7 | 1 | 4 | 17 |
| Placebo | D56 | 17 | 1.3 | 8.9 | 2.2 | −20 | −2 | 0 | 6 | 19 |

A similar evaluation of the differences in the raw data measurements provided in Table 15, show that the changes in mean total cholesterol levels did not fluctuate more than approximately 0.05 X/X that were within the Standard Error of the Mean range. See, Table 19.

TABLE 19

Raw Value Change of Total Cholesterol levels at Study Day 56 as compared to Baseline (Sudy Day 0)

| Treatment | −VISIT | N | MEAN | SD | SE | MIN | Q1 | MEDIAN | Q3 | MAX |
|---|---|---|---|---|---|---|---|---|---|---|
| All | D56 | 35 | 0.01 | 0.54 | 0.09 | −1.2 | −0.3 | 0.0 | 0.3 | 1.1 |
| Krill Powder | D56 | 18 | −0.03 | 0.58 | 0.14 | −1.1 | −0.3 | 0.1 | 0.2 | 1.1 |
| Placebo | D56 | 17 | 0.05 | 0.51 | 0.12 | −1.2 | −0.2 | 0.0 | 0.3 | 1.0 |

F. Triglyceride Results

Triglyceride levels were seen not to be appreciably altered when comparing the Krill Powder group to the Placebo group over the duration of the study period. See, Table 20.

TABLE 20

Triglyceride Levels Over the Study Period

| Treatment | VISIT | N | MEAN | SD | SE | MIN | Q1 | MEDIAN | Q3 | MAX |
|---|---|---|---|---|---|---|---|---|---|---|
| All | BAS | 35 | 1.30 | 0.54 | 0.09 | 0.4 | 0.9 | 1.2 | 1.5 | 2.6 |
|  | D28 | 35 | 1.34 | 0.68 | 0.11 | 0.6 | 0.9 | 1.2 | 1.7 | 3.4 |
|  | D56 | 35 | 1.35 | 0.60 | 0.10 | 0.4 | 0.9 | 1.2 | 1.7 | 2.9 |
| Krill Powder | BAS | 18 | 1.31 | 0.49 | 0.12 | 0.4 | 1.0 | 1.2 | 1.5 | 2.5 |
|  | D28 | 18 | 1.42 | 0.83 | 0.20 | 0.6 | 0.9 | 1.1 | 1.7 | 3.4 |
|  | D56 | 18 | 1.45 | 0.72 | 0.17 | 0.4 | 0.9 | 1.5 | 1.8 | 2.9 |
| Placebo | BAS | 17 | 1.29 | 0.61 | 0.15 | 0.6 | 0.9 | 1.1 | 1.5 | 2.6 |
|  | D28 | 17 | 1.25 | 0.48 | 0.12 | 0.7 | 0.9 | 1.2 | 1.5 | 2.4 |
|  | D56 | 17 | 1.24 | 0.44 | 0.11 | 0.6 | 0.9 | 1.2 | 1.6 | 2.1 |

BAS = Baseline at Study Day 0;
D28 = Study Day 28;
D56 = Study Day 56

When each group at Study Day 28 was compared to its respective baseline, each group reflected mean differences of triglyceride levels that were approximately 9.0% or less that were within the Standard Error of the Mean range. See, Table 21.

TABLE 21

Percentage Change Of Total Cholesterol levels at Study Day 28 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | 7.2 | 36.0 | 6.1 | −54 | −24 | −1 | 28 | 91 |
| Krill Powder | D28 | 18 | 9.0 | 41.1 | 9.7 | −38 | −28 | −3 | 39 | 91 |
| Placebo | D28 | 17 | 5.3 | 30.7 | 7.5 | −54 | −16 | 1 | 23 | 70 |

A similar evaluation of the differences in the raw data measurements provided in Table 20, show that the changes in mean triglyceride levels did not fluctuate more than approximately 0.11 X/X that were within the Standard Error of the Mean range. See, Table 22.

TABLE 22

Raw Value Change of Triglyceride levels at Study Day 28 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D28 | 35 | 0.04 | 0.48 | 0.08 | −1.4 | −0.3 | −0.0 | 0.3 | 1.0 |
| Krill Powder | D28 | 18 | 0.11 | 0.51 | 0.12 | −0.5 | −0.3 | −0.0 | 0.5 | 1.0 |
| Placebo | D28 | 17 | −0.03 | 0.44 | 0.11 | −1.4 | −0.2 | 0.0 | 0.3 | 0.5 |

When each group at Study Day 56 was compared to its respective baseline, each group reflected mean differences of triglyceride levels that were approximately 10.0% or less that were near or within the Standard Error of the Mean range. See, Table 23.

TABLE 23

Percentage Change Of Triglyceride levels at Study Day 56 as compared to Baseline (Study Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 8.2 | 35.3 | 6.0 | −55 | −17 | 6 | 24 | 90 |
| Krill Powder | D56 | 18 | 10.0 | 34.3 | 8.1 | −36 | −8 | 3 | 24 | 90 |
| Placebo | D56 | 17 | 6.4 | 37.3 | 9.0 | −55 | −28 | 6 | 18 | 79 |

A similar evaluation of the differences in the raw data measurements provided in Table 20, show that the changes in mean triglyceride levels did not fluctuate more than approximately 0.14 X/X that were near or within the Standard Error of the Mean range. See, Table 24.

TABLE 24

Raw Value Change of Triglyceride levels at Study Day 56 as compared to Baseline (Sudy Day 0)

| Treatment | VISIT | N | MEAN | SD | SE | MIN | Q1 | MEDIAN | Q3 | MAX |
|---|---|---|---|---|---|---|---|---|---|---|
| All | D56 | 35 | 0.05 | 0.47 | 0.08 | −1.4 | −0.2 | 0.1 | 0.3 | 1.3 |
| Krill powder | D56 | 18 | 0.14 | 0.43 | 0.10 | −0.4 | −0.1 | 0.0 | 0.3 | 1.3 |
| Placebo | D56 | 17 | −0.05 | 0.51 | 0.12 | −1.4 | −0.3 | 0.1 | 0.3 | 0.5 |

F. Diastolic Blood Pressure Results

Diastolic blood pressure was observed to have a time-related reduction over the study period in the Krill Powder group as compared to the Placebo group (e.g., 88.58 to 85.56 mmHg versus 86.47 to 86.35). See, Table 25.

TABLE 25

Diastolic Blood Pressure Over the Study Period

| Treatment | VISIT | N | MEAN | SD | SE | MIN | Q1 | MEDIAN | Q3 | MAX |
|---|---|---|---|---|---|---|---|---|---|---|
| All | SCR | 35 | 87.56 | 7.57 | 1.28 | 70.5 | 83.0 | 87.0 | 92.0 | 100.0 |
|  | BAS | 35 | 87.16 | 6.90 | 1.17 | 72.0 | 82.0 | 87.0 | 93.0 | 100.0 |
|  | V4 | 35 | 85.84 | 9.10 | 1.54 | 63.5 | 80.5 | 87.0 | 93.5 | 103.0 |
|  | V5 | 35 | 84.43 | 8.48 | 1.43 | 67.5 | 77.0 | 84.5 | 89.0 | 104.0 |
|  | V6 | 35 | 85.94 | 8.47 | 1.43 | 71.5 | 80.5 | 86.0 | 90.0 | 112.5 |
| Krill Powder | SCR | 18 | 88.58 | 7.00 | 1.65 | 74.5 | 83.5 | 88.8 | 92.0 | 100.0 |
|  | BAS | 18 | 88.61 | 7.68 | 1.81 | 72.0 | 82.0 | 89.5 | 95.0 | 100.0 |
|  | V4 | 18 | 85.53 | 10.61 | 2.50 | 63.5 | 78.0 | 87.0 | 93.5 | 103.0 |
|  | V5 | 18 | 87.00 | 9.46 | 2.23 | 67.5 | 80.0 | 87.3 | 93.0 | 104.0 |
|  | V6 | 18 | 85.56 | 7.90 | 1.86 | 71.5 | 81.0 | 84.5 | 90.0 | 104.5 |
| Placebo | SCR | 17 | 86.47 | 8.21 | 1.99 | 70.5 | 83.0 | 85.0 | 92.0 | 99.5 |
|  | BAS | 17 | 85.62 | 5.79 | 1.40 | 73.5 | 82.5 | 87.0 | 89.0 | 96.0 |
|  | V4 | 17 | 86.18 | 7.50 | 1.82 | 73.0 | 82.0 | 86.0 | 89.5 | 99.0 |
|  | V5 | 17 | 81.71 | 6.51 | 1.58 | 70.0 | 76.5 | 82.5 | 86.0 | 92.0 |
|  | V6 | 17 | 86.35 | 9.26 | 2.25 | 74.5 | 80.5 | 87.0 | 88.0 | 112.5 |

SCR—Prescreening Visit;
BAS—Baseline Study Day 0;
V4—Visit 4;
V5—Visit 5;
V6—Visit 6.

When each group at V4 was compared to its respective baseline, the Krill Powder group showed and approximate four-fold change in blood pressure as compared to the Placebo group. For example, the Krill Powder group showed a reduction of 3.4% and the Placebo group showed an increase of 0.8%. See, Table 26.

TABLE 26

Percent Change Of Diastolic Blood Pressure On Visit 4

| Treatment | VISIT | N | MEAN | SD | SE | MIN | Q1 | MEDIAN | Q3 | MAX |
|---|---|---|---|---|---|---|---|---|---|---|
| All | V4 | 35 | −1.4 | 8.4 | 1.4 | −25 | −8 | 1 | 3 | 14 |
| Krill Powder | V4 | 18 | −3.4 | 9.1 | 2.1 | −25 | −9 | −2 | 3 | 11 |
| Placebo | V4 | 17 | 0.8 | 7.4 | 1.8 | −14 | −2 | 2 | 4 | 14 |

A similar evaluation of the differences in the raw data measurements provided in Table 25, show that the changes in mean diastolic pressure decrease by 3.08 mmHg in the Krill Powder group as opposed to an increase of 0.56 mmHg in the Placebo group. See, Table 27.

TABLE 27

Raw Value Change of Diastolic Blood Pressure at Visit 4

| Treatment | VISIT | N | MEAN | SD | SE | MIN | Q1 | MEDIAN | Q3 | MAX |
|---|---|---|---|---|---|---|---|---|---|---|
| All | V4 | 35 | −1.31 | 7.42 | 1.25 | −21.0 | −7.0 | 1.0 | 3.0 | 12.0 |
| Krill Powder | V4 | 18 | −3.08 | 7.99 | 1.88 | −21.0 | −8.5 | −1.5 | 2.5 | 10.0 |
| Placebo | V4 | 17 | 0.56 | 6.47 | 1.57 | −13.5 | −2.0 | 1.5 | 3.0 | 12.0 |

When each group at V5 was compared to its respective baseline, there was no appreciable difference between the Krill Powder group versus the Placebo group as the mean changes in diastolic blood pressure were within the Standard Error Of The Mean ranges. See, Table 28.

TABLE 28

| | | | | Percent Change Of Diastolic Blood Pressure On Visit 5 | | | | | |
|---|---|---|---|---|---|---|---|---|---|
| Treatment | VISIT | N | MEAN | SD | SE | MIN | Q1 | MEDIAN | Q3 | MAX |
| All | V5 | 35 | −3.2 | 5.4 | 0.9 | −12 | −8 | −4 | 2 | 7 |
| Krill Powder | V5 | 18 | −1.9 | 5.7 | 1.3 | −10 | −6 | −2 | 3 | 7 |
| Placebo | V5 | 17 | −4.5 | 4.8 | 1.2 | −12 | −8 | −5 | −1 | 5 |

A similar evaluation of the differences in the raw data measurements on V5 as provided in Table 25, show that the reduction in mean diastolic pressure decrease in the Krill Powder group was less than in the Placebo group. See, Table 29.

TABLE 29

| | | | | Raw Value Change of Diastolic Blood Pressure at Visit 5 | | | | | |
|---|---|---|---|---|---|---|---|---|---|
| Treatment | VISIT | N | MEAN | SD | SE | MIN | Q1 | MEDIAN | Q3 | MAX |
| All | V5 | 35 | −2.73 | 4.83 | 0.82 | −10.5 | −7.5 | −3.0 | 1.5 | 6.0 |
| Krill powder | V5 | 18 | −1.61 | 5.15 | 1.21 | −10.0 | −4.5 | −1.5 | 3.0 | 6.0 |
| Placebo | V5 | 17 | −3.91 | 4.30 | 1.04 | −10.5 | −7.5 | −3.5 | −1.0 | 4.0 |

When each group at V6 was compared to its respective baseline, there was and approximate four-fold difference between the Krill Powder group versus the Placebo group (e.g., −3.3% versus +0.9%). See, Table 30.

TABLE 30

| | | | | Percent Change Of Diastolic Blood Pressure On Visit 6 | | | | | |
|---|---|---|---|---|---|---|---|---|---|
| Treatment | VISIT | N | MEAN | SD | SE | MIN | Q1 | MEDIAN | Q3 | MAX |
| All | V6 | 35 | −1.2 | 7.7 | 1.3 | −15 | −7 | −2 | 3 | 20 |
| Krill Powder | V6 | 18 | −3.3 | 6.7 | 1.6 | −15 | −8 | −4 | 1 | 10 |
| Placebo | V6 | 17 | 0.9 | 8.3 | 2.0 | −10 | −4 | −1 | 4 | 20 |

A similar evaluation of the differences in the raw data measurements on V6 as provided in Table 25, show that the reduction in mean diastolic pressure decrease of 3.06 mmHG in the Krill Powder group versus an increase of 0.74 mmHg in the Placebo group. See, Table 31.

TABLE 31

| | | | | Raw Value Change Of Diastolic Blood Pressure (mmHg) On Visit 6 | | | | | |
|---|---|---|---|---|---|---|---|---|---|
| Treatment | VISIT | N | MEAN | SD | SE | MIN | Q1 | MEDIAN | Q3 | MAX |
| All | V6 | 35 | −1.21 | 6.93 | 1.17 | −14.5 | −6.5 | −2.0 | 2.0 | 19.0 |
| Krill powder | V6 | 18 | −3.06 | 6.11 | 1.44 | −14.5 | −7.0 | −3.3 | 0.5 | 9.5 |
| Placebo | V6 | 17 | 0.74 | 7.40 | 1.79 | −9.0 | −3.5 | −0.5 | 3.0 | 19.0 |

G. Systolic Blood Pressure Results

Diastolic blood pressure was observed to have a time-related reduction over the study period in the Krill Powder group as compared to the Placebo group (e.g., 141.39 to 133.97 mmHg versus 138.59 to 134.26). See, Table 32.

TABLE 32

Systolic Blood Pressure Over the Study Period

| Treatment | VISIT | N | MEAN | SD | SE | MIN | Q1 | MEDIAN | Q3 | MAX |
|---|---|---|---|---|---|---|---|---|---|---|
| All | SCR | 35 | 140.03 | 8.87 | 1.50 | 125.5 | 133.0 | 140.5 | 146.0 | 161.5 |
| | BAS | 35 | 138.69 | 8.52 | 1.44 | 122.5 | 132.0 | 138.5 | 145.0 | 155.5 |
| | V4 | 35 | 135.21 | 13.06 | 2.21 | 108.5 | 129.0 | 133.5 | 141.5 | 172.0 |
| | V5 | 35 | 129.54 | 11.16 | 1.89 | 111.0 | 122.0 | 127.5 | 137.0 | 155.5 |
| | V6 | 35 | 134.11 | 12.14 | 2.05 | 109.0 | 125.0 | 133.5 | 143.5 | 158.0 |
| Krill Powder | SCR | 18 | 141.39 | 8.61 | 2.03 | 125.5 | 134.5 | 142.8 | 148.0 | 156.5 |
| | BAS | 18 | 141.78 | 8.67 | 2.04 | 125.5 | 134.0 | 143.5 | 148.5 | 155.5 |
| | V4 | 18 | 134.08 | 14.35 | 3.38 | 108.5 | 126.0 | 135.3 | 143.0 | 158.5 |
| | V5 | 18 | 134.22 | 12.37 | 2.92 | 111.0 | 124.5 | 133.5 | 144.0 | 155.5 |
| | V6 | 18 | 133.97 | 13.00 | 3.06 | 109.0 | 126.0 | 133.0 | 139.0 | 158.0 |
| Placebo | SCR | 17 | 138.59 | 9.17 | 2.22 | 125.5 | 131.0 | 138.5 | 145.0 | 161.5 |
| | BAS | 17 | 135.41 | 7.22 | 1.75 | 122.5 | 131.5 | 132.0 | 142.5 | 147.0 |
| | V4 | 17 | 136.41 | 11.86 | 2.88 | 116.0 | 130.5 | 133.5 | 139.0 | 172.0 |
| | V5 | 17 | 124.59 | 7.18 | 1.74 | 114.5 | 118.0 | 125.5 | 130.5 | 137.0 |
| | V6 | 17 | 134.26 | 11.56 | 2.80 | 114.5 | 122.5 | 134.0 | 144.0 | 150.5 |

SCR - Prescreening Visit;
BAS—Baseline Study Day 0;
V4—Visit 4;
V5—Visit 5;
V6—Visit 6.

When each group at V4 was compared to its respective baseline, the Krill Powder group showed and approximate six-fold change in systolic blood pressure as compared to the Placebo group. For example, the Krill Powder group showed a reduction of 5.5% and the Placebo group showed an increase of 1.0%. See, Table 33.

TABLE 33

Percent Change Of Systolic Blood Pressure On Visit 4

| Treatment | VISIT | N | MEAN | SD | SE | MIN | Q1 | MEDIAN | Q3 | MAX |
|---|---|---|---|---|---|---|---|---|---|---|
| All | V4 | 35 | −2.3 | 9.6 | 1.6 | −19 | −9 | −2 | 3 | 30 |
| Krill Powder | V4 | 18 | −5.5 | 7.9 | 1.9 | −18 | −11 | −4 | 0 | 6 |
| Placebo | V4 | 17 | 1.0 | 10.4 | 2.5 | −19 | −4 | 0 | 4 | 30 |

A similar evaluation of the differences in the raw data measurements on V4 as provided in Table 32, show a reduction in mean systolic pressure decrease of 7.69 mmHg in the Krill Powder group versus an increase of 1.00 mmHg in the Placebo group. See, Table 34.

TABLE 34

Raw Value Change Of Systolic Blood Pressure (mmHg) On Visit 4

| Treatment | VISIT | N | MEAN | SD | SE | MIN | Q1 | MEDIAN | Q3 | MAX |
|---|---|---|---|---|---|---|---|---|---|---|
| All | V4 | 35 | −3.47 | 13.22 | 2.23 | −26.5 | −14.0 | −2.0 | 4.0 | 40.0 |
| Krill powder | V4 | 18 | −7.69 | 11.16 | 2.63 | −26.5 | −16.5 | −5.0 | 0.5 | 8.5 |
| Placebo | V4 | 17 | 1.00 | 14.06 | 3.41 | −26.5 | −5.5 | 0.5 | 5.5 | 40.0 |

When each group at V5 was compared to its respective baseline, the Krill Powder group showed no appreciable differences as compared to the Placebo group as the means were within or near the Standard Error of the Mean ranges. See, Table 35.

TABLE 35

Percent Change Of Systolic Blood Pressure On Visit 5

| Treatment | VISIT | N | MEAN | SD | SE | MIN | Q1 | MEDIAN | Q3 | MAX |
|---|---|---|---|---|---|---|---|---|---|---|
| All | V5 | 35 | −6.5 | 6.3 | 1.1 | −20 | −12 | −6 | −4 | 5 |
| Krill powder | V5 | 18 | −5.4 | 6.0 | 1.4 | −15 | −12 | −6 | −0 | 5 |
| Placebo | V5 | 17 | −7.8 | 6.7 | 1.6 | −20 | −12 | −6 | −5 | 4 |

A similar evaluation of the differences in the raw data measurements on V5 as provided in Table 32, showed near equivalent reductions in mean systolic pressure between the Krill Powder group and the Placebo group. See, Table 36.

TABLE 36

Raw Value Change Of Systolic Blood Pressure (mmHg) On Visit 5

| Treatment | VISIT | N | MEAN | SD | SE | MIN | Q1 | MEDIAN | Q3 | MAX |
|---|---|---|---|---|---|---|---|---|---|---|
| All | V5 | 35 | −9.14 | 9.00 | 1.52 | −29.0 | −16.0 | −8.0 | −5.5 | 7.0 |
| Krill powder | V5 | 18 | −7.56 | 8.41 | 1.98 | −21.5 | −14.5 | −7.5 | −0.5 | 7.0 |
| Placebo | V5 | 17 | −10.82 | 9.54 | 2.31 | −29.0 | −16.5 | −8.5 | −6.0 | 5.0 |

When each group at V6 was compared to its respective baseline, the Krill Powder group showed an approximate five-fold reduction in systolic blood pressure as compared to the Placebo group (e.g., 5.5% decrease versus 0.7% decrease). See, Table 37.

TABLE 37

Percent Change Of Systolic Blood Pressure On Visit 6

| Treatment | VISIT | N | MEAN | SD | SE | MIN | Q1 | MEDIAN | Q3 | MAX |
|---|---|---|---|---|---|---|---|---|---|---|
| All | V6 | 35 | −3.2 | 7.6 | 1.3 | −25 | −7 | −3 | 1 | 14 |
| Krill powder | V6 | 18 | −5.5 | 6.3 | 1.5 | −25 | −8 | −6 | −1 | 3 |
| Placebo | V6 | 17 | −0.7 | 8.2 | 2.0 | −16 | −7 | −0 | 3 | 14 |

A similar evaluation of the differences in the raw data measurements on V6 as provided in Table 32, showed a reduction in mean systolic pressure of 7.81 mmHg in the Krill Powder group versus a 1.15 mmHg reduction the Placebo group. See, Table 38.

TABLE 38

Raw Value Change Of Systolic Blood Pressure (mmHg) On Visit 5

| Treatment | VISIT | N | MEAN | SD | SE | MIN | Q1 | MEDIAN | Q3 | MAX |
|---|---|---|---|---|---|---|---|---|---|---|
| All | V6 | 35 | −4.57 | 10.54 | 1.78 | −35.5 | −10.0 | −5.0 | 2.0 | 19.0 |
| Krill powder | V6 | 18 | −7.81 | 9.08 | 2.14 | −35.5 | −11.0 | −8.5 | −2.0 | 4.5 |
| Placebo | V6 | 17 | −1.15 | 11.14 | 2.70 | −22.5 | −9.0 | −0.5 | 4.5 | 19.0 |

H. Body Weight Results

Body weight was not observed to change appreciably over the study period in either the Krill Powder group or the Placebo group. See, Table 39.

TABLE 39

Body Wieght (Kgs) Over the Study Period

| Treatment | VISIT | N | MEAN | SD | SE | MIN | Q1 | MEDIAN | Q3 | MAX |
|---|---|---|---|---|---|---|---|---|---|---|
| All | SCR | 35 | 84.27 | 10.39 | 1.76 | 66.6 | 76.8 | 84.2 | 89.1 | 114.5 |
|  | BAS | 35 | 84.23 | 10.39 | 1.76 | 66.5 | 76.5 | 84.0 | 89.0 | 115.0 |
|  | V5 | 34 | 84.13 | 10.73 | 1.84 | 66.6 | 75.8 | 83.4 | 88.6 | 115.0 |
|  | V6 | 32 | 84.64 | 10.98 | 1.94 | 66.6 | 76.8 | 84.2 | 91.0 | 116.5 |
| Krill Powder | SCR | 18 | 83.78 | 9.00 | 2.12 | 66.6 | 76.8 | 84.6 | 88.6 | 100.5 |
|  | BAS | 18 | 83.79 | 8.95 | 2.11 | 66.5 | 76.5 | 84.2 | 88.2 | 100.9 |
|  | V5 | 18 | 83.79 | 9.04 | 2.13 | 67.7 | 75.3 | 84.0 | 87.7 | 101.5 |
|  | V6 | 15 | 83.80 | 9.39 | 2.43 | 67.5 | 75.0 | 83.5 | 88.4 | 101.3 |
| Placebo | SCR | 17 | 84.79 | 11.94 | 2.90 | 67.7 | 77.8 | 84.2 | 90.7 | 114.5 |
|  | BAS | 17 | 84.69 | 11.98 | 2.91 | 67.5 | 78.1 | 84.0 | 91.0 | 115.0 |
|  | V5 | 16 | 84.52 | 12.66 | 3.16 | 66.6 | 76.4 | 83.3 | 90.9 | 115.0 |
|  | V6 | 17 | 85.39 | 12.46 | 3.02 | 66.6 | 77.6 | 84.9 | 91.4 | 116.5 |

SCR - Prescreening Visit;
BAS—Baseline Study Day 0;
V5—Visit 5;
V6—Visit 6.

When each group at V5 was compared to its respective baseline, the Krill Powder group showed 0% change in body weight as compared to a 0.3% change in the Placebo group. See, Table 40.

TABLE 40

Percent Change Of Body Wieght On Visit 5

| Treatment | VISIT | N | MEAN | SD | SE | MIN | Q1 | MEDIAN | Q3 | MAX |
|---|---|---|---|---|---|---|---|---|---|---|
| All | V5 | 34 | 0.1 | 1.1 | 0.2 | −2 | −1 | 0 | 1 | 2 |
| Krill Powder | V5 | 18 | −0.0 | 0.9 | 0.2 | −2 | −1 | −0 | 1 | 2 |
| Placebo | V5 | 16 | 0.3 | 1.3 | 0.3 | −1 | −1 | 0 | 1 | 2 |

A similar evaluation of the differences in the raw data measurements on V5 as provided in Table 39, showed a reduction in body weight of 0.01 Kg in the Krill Powder group versus an increase of 0.31 Kg the Placebo group. See, Table 41.

TABLE 41

Raw Value Change Of Body Wieght (Kg) On Visit 5

| Treatment | VISIT | N | MEAN | SD | SE | MIN | Q1 | MEDIAN | Q3 | MAX |
|---|---|---|---|---|---|---|---|---|---|---|
| All | V5 | 34 | 0.14 | 0.88 | 0.15 | −1.3 | −0.6 | 0.0 | 0.6 | 2.1 |
| Krill Powder | V5 | 18 | −0.01 | 0.72 | 0.17 | −1.3 | −0.6 | −0.1 | 0.6 | 1.2 |
| Placebo | V5 | 16 | 0.31 | 1.03 | 0.26 | −1.1 | −0.4 | 0.1 | 0.9 | 2.1 |

When each group at V6 was compared to its respective baseline, the Krill Powder group showed 0% change in body weight as compared to a 0.8% change in the Placebo group. See, Table 42.

TABLE 42

Percent Change Of Body Wieght On Visit 6

| Treatment | VISIT | N | MEAN | SD | SE | MIN | Q1 | MEDIAN | Q3 | MAX |
|---|---|---|---|---|---|---|---|---|---|---|
| All | V6 | 32 | 0.4 | 1.4 | 0.3 | −3 | −1 | 0 | 1 | 3 |
| Krill Powder | V6 | 15 | −0.0 | 1.3 | 0.3 | −3 | −1 | 0 | 1 | 2 |
| Placebo | V6 | 17 | 0.8 | 1.5 | 0.4 | −1 | −1 | 1 | 1 | 3 |

A similar evaluation of the differences in the raw data measurements on V6 as provided in Table 39, showed a reduction in body weight of 0.04 Kg in the Krill Powder group versus an increase of 0.69 Kg the Placebo group. See, Table 43.

TABLE 43

Raw Value Change Of Body Wieght (Kg) On Visit 6

| Treatment | VISIT | N | MEAN | SD | SE | MIN | Q1 | MEDIAN | Q3 | MAX |
|---|---|---|---|---|---|---|---|---|---|---|
| All | V6 | 32 | 0.35 | 1.22 | 0.22 | −3.0 | −0.5 | 0.3 | 1.1 | 2.9 |
| Krill powder | V6 | 15 | −0.04 | 1.13 | 0.29 | −3.0 | −0.5 | 0.2 | 0.6 | 1.5 |
| Placebo | V6 | 17 | 0.69 | 1.23 | 0.30 | −0.9 | −0.5 | 0.4 | 1.5 | 2.9 |

IV. Methods of Making Krill Powder Compositions

There are a number of problems associated with these conventionally known technologies of extracting krill lipids, including but not limited to, a whole crustacean biomass that contains high fluoride exoskeleton particles that results in the production of fluoride-contaminated crustacean biomass. Specifically, brown color can arise from degradation of astaxanthin and/or from accumulation of the end products of non-enzymatic browning (e.g., Strecker degradation products or polymerized pyrroles). Brown color resulting from this non-enzymatic process is believed to result from oxidative degradation due to a reaction of secondary lipid oxidation products with amino groups from amino acids or proteins creating so-called tertiary oxidation products; iii) freezing the crustacean biomass for transportation to an extraction plant. Frozen crustacean biomass can be relatively stable, but some changes in the product are known to occur over time. For example, one characteristic change in frozen krill is partial hydrolysis of the lipids resulting in accumulation of free fatty acids (FFA) arising from both triglycerides and phospholipids and lysophospholipids, specifically lysophosphatidylcholine (LPC), arising from hydrolysis of phosphatidylcholine; iv) the use of heat and frozen storage can induce oxidation of lipids and proteins in crustacean biomass.

The invention relates to a method for processing crustaceans (i.e., for example, krill) rich in lipids to produce krill powder compositions comprising phospholipids, proteinaceous nutrients and oil (i.e., for example, neutral lipids and/or triglycerides) and that are low in fluoride content.

In some embodiments, the present invention contemplates methods of processing crustacean biomass having unexpected findings including, but not limited to: i) removal of most of the exoskeleton from the crustacean biomass that results in low level of fluorides in a phospholipid-protein complex (PPC) that is processed into a krill powder that has a reddish color suggesting that minimal degradation of astaxanthin or formation of tertiary oxidation products has occurred; These findings suggest that the proteins and/or lipids of crustacean biomass have undergone minimal hydrolysis during the initial processing steps producing PPC.

Such krill powder has recently been reported to have long term. Krill is a valuable sustainable resource of omega-3 fatty acids and protein, which may be processed into a krill powder for human consumption. The stability of krill powder was assessed when stored for up to 12 months at room temperature. In addition, the effect of packaging in vacuum was observed. The stability was assessed by changes in concentrations of lipid classes, antioxidants, pyrroles and lipid, and Strecker-derived volatiles. Some degradation occurred during storage at room temperature. Thus, a minor increase in volatiles, an increase in free fatty acids and a concomitant decrease in antioxidants, tocopherol, and astaxanthin was observed. In addition, there was a minor decrease in phospholipids and n-3 fatty acids; however, storage at vacuum improved the oxidative stability of krill powder. The data shows stability during storage up to 12 months at room temperature while vacuum-packed. Nielsen et al., "Quality Changes Of Antarctic Krill Powder During Long Term Storage" *Eur J Lipid Science and Tech* Vol 118 (2016).

In one embodiment, the present invention contemplates a method comprising forming a phospholipid-peptide complex (PPC) composition (e.g., a krill powder) from a crustacean (i.e., for example, krill) immediately after the catch has been brought upon on board a boat and/or ship (i.e., for example, a fishing vessel). The process of creating the PPC composition comprises disintegrating the crustaceans into a disintegrated material comprising smaller particles (i.e., for example, between approximately 1-25 millimeters), adding water, heating the disintegrated material, adding enzyme(s) to hydrolyze the disintegrated material, deactivating the enzyme(s), removing solids (i.e., for example, exoskeleton, shell, and/or carapace) from the enzymatically processed material to reduce the fluoride content of the material, separating and drying the PPC composition to create the krill powder. An advantage of some embodiments of the invention is that these crustacean products have a low fluoride content. This is due to the fact that the solid crustacean exoskeletal particles (i.e., for example, shell and/or carapace) are effectively removed from mass to be processed. The present invention provides an industrial method for processing catches of crustaceans comprising a number of steps beginning with a very early and substantially complete removal of the crustacean's exoskeleton (i.e., for example, the crust, carapace and/or shell). Although it is not necessary to understand the mechanism of an invention, it is believed that the crustacean exoskeleton comprises a vast majority of fluoride in the organism. Consequently, this step thereby results in a substantial removal of fluoride from the crustacean material. The method also uses longitudinal centrifugation techniques that prevents separation problems caused by emulsions when processing a raw material with high content of phospholipids.

The method according to the present invention is initiated immediately after decking a catch of crustacean. It is of importance that the method according to the present invention is initiated as soon as possible after the crustacean catch has been decked since fluoride starts to leak/diffuse immediately from the exoskeleton into the crustacean's flesh and juices.

When using the term "immediately" in connection with starting the process according to the present invention this relates to the period from decking the crustacean catch and to the initial disintegration of the crustacean (see infra). This period of time should be kept to a minimum, and should preferably not exceed 60 minutes, more preferred not exceed 30 minutes, even more preferred not exceed 15 minutes, and should include a direct transfer of the krill catch from the trawl bag and/or net to a suitable disintegrator. A disintegrator of the crustacean material may be a conventional pulping, milling, grinding or shredding machine.

The crustacean catch is initially loaded into a disintegration apparatus where the crustacean catch is subjected to pulping, milling, grinding and/or shredding to create a disintegrated crustacean material. The temperature of the disintegration process is around the ambient temperature of the water, i.e. between −2 and +1° C., preferably around +0° C. to +6° C., and may be performed by any convenient disintegration method. This disintegration process is also conventionally done by the previous known processing methods, and represents one of the obstacles according to the prior art because it produces large amounts of exoskeletal particles from the crustacean mixing in the milled material and producing a disintegrated paste with a high fluoride content. However, this high fluoride content is one of the reasons why the prior art processed crustacean material has limited applications and is less suitable for food, feed or corresponding food or feed additives compared to other marine raw materials e.g. pelagic fish.

According to the present invention the crustacean material is divided into a particle size suitable for a further separation step for not interfering with the subsequent processing steps. The disintegrating process is performed continuously and produces particle sizes up to 25 mm, a preferred particle size range is between approximately 0.5-10 mm and a more preferred size range is between approximately 1.0-8 mm.

Although it is not necessary to understand the mechanism of an invention, it is believed that this small particle size distribution represents one of advantages of the present invention because the fluoride has a tendency to leak out of the milled material and mingle with the rest of the raw material. However, this leaking process takes time and is not rapid enough to negatively impact a subsequent enzymatic hydrolysis step, provided the hydrolysis step is performed within specific parameters with respect to time and optimal, or near-optimal conditions, such as pH and temperature and optionally with the addition of co-factors such as specific ions depending on the used enzymes.

The temperature of the disintegrated material may, according to the present invention, be elevated to a temperature suitable for the subsequent enzymatic hydrolysis. Preferably, the temperature may be increased within seconds (e.g. 1-300 seconds, more preferred 1-100 seconds, even more preferred 1-60 seconds, most preferred 1-10 seconds) subsequent to the disintegrating step for reducing the processing time and thereby preventing diffusion of fluoride and for preparing the material for the enzymatic hydrolysis.

According to the present invention enzymes may be added directly to the disintegrated material or through the added water or both, before, during or after the disintegration process.

According to the present invention, exogenous proteolytic enzymes (e.g., alkalase, neutrase, enzymes derived from microorganisms including, but not limited to, *Bacillus subtilis* and/or *Aspergillus niger*, and/or or enzymes derived from plant species) may be added before, during or after the disintegration, and before, during or after the heating of the disintegrated material. The added enzyme(s) may be in the form of one single enzyme or a mixture of enzymes. The conditions of the hydrolysis should match the optimal hydrolytic conditions of the added enzyme(s) and the selection of optimal conditions for the selected exogenous hydrolytic enzyme(s) is known to the person skilled in the art. As an example, the exogenous enzyme alkalase having a pH optimum of about 8, a temperature optimum of 60° C. and a hydrolysis time of 40-120 minutes. The selected enzymes, or combination of enzymes, should also be chosen for reducing emulsions caused by high content of phospholipids in the raw material.

An efficient amount of proteolytic enzyme(s) will be set after a process- and product optimization process that depends upon the efficiency of a specific chosen commercial enzyme or mix of enzymes. A typical amount by weight of commercial enzymes, as a ratio of the amount of the weight of the disintegrated raw material, are preferably between 0.5% and 0.05%, more preferably between 0.3% and 0.07% and most preferable between 0.2% and 0.09%. This hydrolysis step is aided by endogenous (natural) enzymes because rapid and uncontrolled autolysis is well known in fresh caught crustaceans.

The reason for adding exogenous enzymes is to take control of, and guide, the breakdown of the proteinaceous material in the disintegrated substance as well as speeding up/accelerating the hydrolysis of the material to avoid and/or preclude the leaking of fluoride from the shell, carapace and crust as mentioned supra. These hydrolytic enzymes, or a combination of hydrolytic enzymes, should also be carefully chosen to reduce emulsion in the production process. Enzymes may be selected from exo- and/or endopeptidases. If a mixture of enzymes is used, such a mixture may also include one or more chitinases for subsequently making the chitin-containing fraction(s) more amenable to further downstream processing. If chitinases are used, care must be taken for not increasing the leakage of fluoride from the shell/crust/carapace of the crustacean into the other fractions. However, since such fluoride leakage takes time, it is possible to perform such an enzymatic treatment within the time parameters indicated supra. A more convenient alternative to including chitinases in the enzyme mix of the initial hydrolysis step will be to process the separated chitin-containing fraction subsequently to the separation step.

As it is important to avoid the leaking of fluoride from the milled exoskeletal material into the milled fleshy material, and since the leaking to some degree is related to the increased surface area created through the disintegrating step, the enzymatic hydrolysis step should be finished within a time interval of 100 minutes, preferably within 60 minutes, most preferred within 45 minutes calculated from the addition of the endogenous enzyme(s). The amount of enzyme(s) added is related to the type of enzyme product used. As an example it may be mentioned that the enzyme alkalase may be added in an amount of 0.1-0.5% (w/w) of the raw material. This should be taken into context with the added endogenous enzymes since the addition of more enzymes will reduce the time interval of the hydrolytic step. As mentioned supra the time of the hydrolytic step is one of the crucial features of the present process since a short hydrolysis time reduces the diffusion time of fluoride from particles of the exoskeleton. The hydrolytic enzymatic processing step is intended to remove the binding between the soft tissue of the krill to the exoskeleton of the crustacean.

Subsequent to, or together with, the hydrolytic processing step the hydrolyzed and disintegrated crustacean material is passed through a particle removal device operating through a gravitational force such as a longitudinal centrifuge (i.e., for example, a decanter). This first separation step removes the fine particles containing a considerable amount of the fluoride from the hydrolysed or hydrolysing crustacean material to create a solids fraction. The centrifuge is operated with a g force between 1,000 and 1,800 g, more preferably between 1,200 and 1,600 g and most preferably between 1,300 and 1,500 g. Through this particle removal step a substantial amount of fluoride is removed from the proteinaceous crustacean fraction. The reduction of fluoride on a dry weight basis as compared to conventional crustacean meal, with a typical fluoride content of 1,500 p.p.m, may be up to 50%, even more preferred up to 85%, most preferred up to 95%.

The enzymatic hydrolysis may be terminated by heating of the hydrolysing material (incubate) to a temperature over 90° C., preferably between 92-98° C. and most preferred between 92-95° C., prior to, during or after the separation step, as long as the hydrolysis duration lies within the above given boundaries. The hydrolysis is terminated before, during, or after the fine particle removal step, most preferred after the fine particle removal step. The temperature of the first centrifugation particle removal step, in one embodiment, depend on the optimal activity temperature of the enzyme (in the case where the enzymatic hydrolysis step is terminated by heating after the fine particle separation step).

The fluoride content in the prior art processed krill protein material has limited applications and are less suitable for food or feed or corresponding food or feed additives, as mentioned supra but the fluoride content of the removed exoskeletal material is not preventive for further separation/purification of this fraction. Thus materials such as chitin, chitosan and astaxanthin may be isolated from the separated exoskeletal material. Such isolation procedures are known within the art. Steps may also be taken for removing the fluoride from the isolated exoskeletal material e.g. through dialysis, nanofiltration, through electrophoresis or other appropriate technologies.

Hydrolytic enzyme(s) deactivation may be performed in different ways, such as adding inhibitors, removing co-factors (e.g., crucial ions through dialysis), through thermal inactivation and/or by any other deactivating means. Among these, thermal inactivation, as mentioned supra, is preferred by heating the proteinaceous material to a temperature where the hydrolytic enzymes become denatured and deactivated. However, if a product where the relevant native proteins are not denatured is wanted, other means than heating for deactivating the hydrolytic enzymes should be selected.

A first centrifugation forms a de-fluorinated hydrolyzed and disintegrated crustacean material fraction and a solids fraction (e.g., containing high fluoride exoskeleton particles). As described below, the low flourine hydrolyzed and disintegrated crustacean material fraction may be subsequently separated (e.g., by a second centrifugation) to form a low fluoride Phospholipid-Peptide Complex (PPC) composition fraction, a lean low fluoride Concentrated Hydrolysate Fraction (CHF) fraction that can be used as a food and/or feed additives, and a lipid fraction mainly consisting of neutral lipids. The PPC composition subfraction is rich in lipids, like a smooth cream with no particles, wherein the lipids are well suspended within the peptide components. This suspension results in small density differences between the different PPC composition components thereby making it difficult to further separate the PPC composition with common centrifugal separators and/or decanters. This is especially accentuated with crustacean catches during the second half of the fishing season.

Ordinary disc centrifugal separators (i.e., generating rotational force in the X and Y plane) do not work properly to separate a PPC composition subfraction into its respective components since emptying and necessary cleaning cycles with water will disturb separation zones. Conventional centrifugation separation processes result in the formation of unwanted emulsion products having a high phospholipid content and low dry matter concentrations. Standard decanters cannot separate the PPC composition subfraction into its respective components due to a low g force limitation, short separation zone and an intermixing of light and heavy phases at the discharge of heavy phase from the machine.

Figure 2:
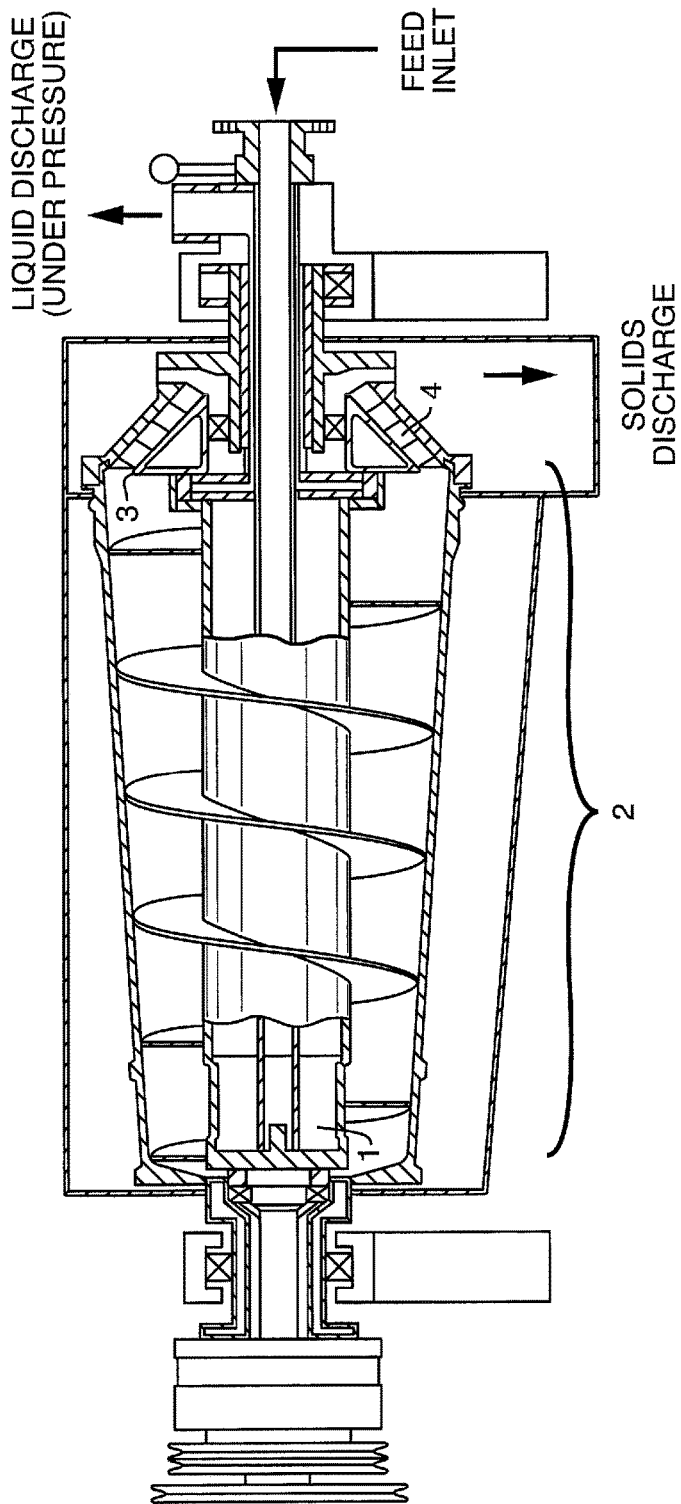
FIG. 2 presents a longitudinal centrifuge with an extended separation path. This specific example is a FLOTTWEG SEDICANTER horizontal decanter centrifuge.
Figure 3:
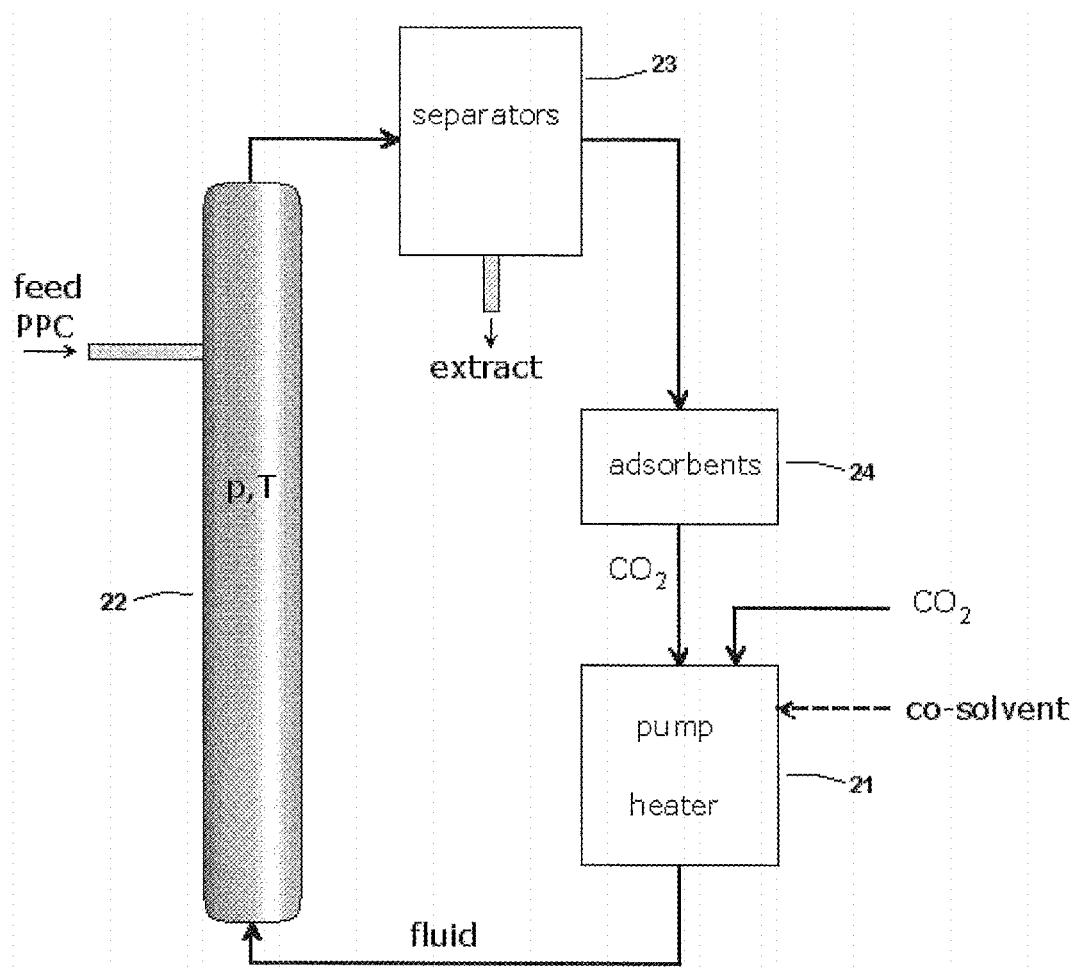
FIG. 3 depicts one example of an extraction plant suitable for use in the presently disclosed method. For example, the plant comprises a solvent unit (21), an extraction tank (22), separators (23) and adsorbents (24).
Figure 4:
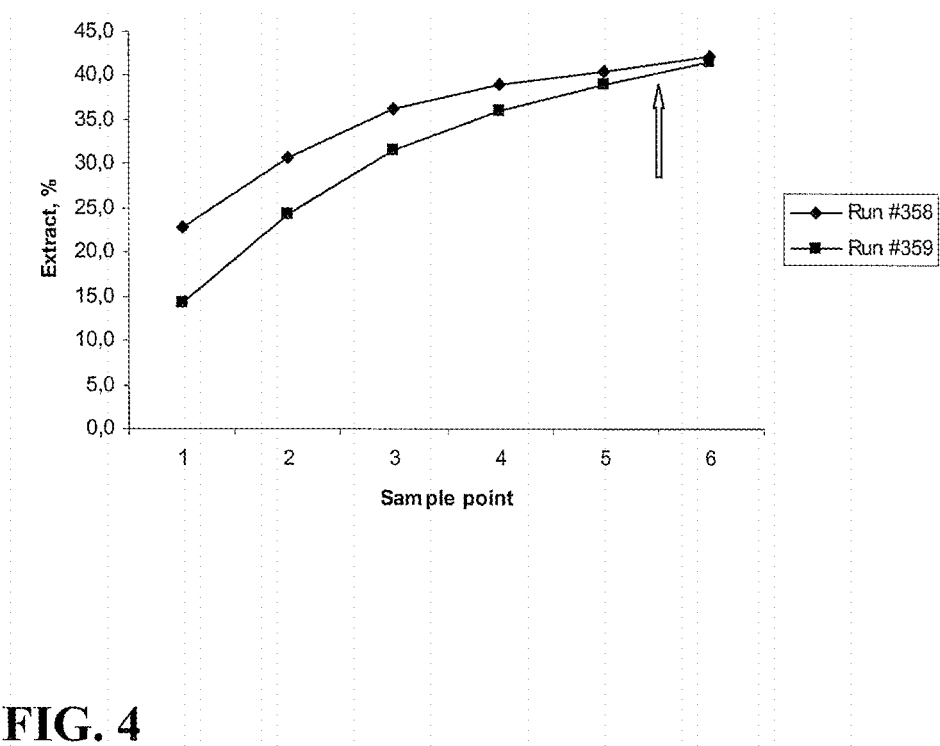
FIG. 4 present exemplary data showing the extraction efficiencies of two different runs in accordance with one embodiment of the present invention.

In one embodiment, the present invention contemplates a method comprising separating a low fluoride PPC material into subfractions using a horizontal decanter centrifuge with an extended separation path. See, FIG. 2. Horizontal centrifuges (e.g., generating a rotational force in the Z plane) are useful for the present invention comprise modified conventional decanter centrifuges. For example, a PPC composition subfraction would enter an ordinary decanter from a bowl through a central placed feed pipe in the middle of the separation zone. In contrast, when using horizontal centrifuges as contemplated herein, the PPC composition subfraction enters at the end and at the opposite side of the outlet (1). This modification provides a significant improvement in the separation process by providing a considerably longer clarification/separation zone than ordinary decanters and utilizes the total available separation length (2) of the machine. The drive is able to impart high g-forces: 10,000 g for small machines and 5,000 to 6,000 g for high capacity machines, facilitating the separation of very fine, slow-settling PPC composition subfractions without the complications of emulsification. The PPC composition subfraction will be subjected to the highest g-force just before entering under the baffle (3). The different liquid layers separated from PPC composition subfraction are concentrated gradually along the axis of the horizontal centrifuge thereby exiting the machine under baffle (3) by the g force pressure generated by the machine (4). The separation of the PPC composition subfraction into a layer comprising about 27-30% dry matter makes the downstream processing efficient in terms of operating/robustness and as well economically considering both yield and costs of preparing the dry matter into a meal composition. The PPC composition subfraction separation also creates a layer comprising a lean hydrolysate that can be evaporated into a concentrated hydrolysate of greater than 60%.

The PPC composition may then be dried into a krill powder for use as contemplated by the present invention. For example, the PPC material is dried to a meal to avoid the lipid oxidation. The drying process is gentle with low temperature (0-15° C., preferably 2-8° C.) and inert conditions, which give a reduced oxidative stress on the long-chain poly-unsaturated omega-3 fatty acids. A lyophilisation process would also be suitable since this avoids an overheating of the product. The PPC material (e.g., krill powder) is then packed in air tight bags under nitrogen atmosphere for later direct use and continuation processes.

A typical mass balance of the processed raw lean Antarctic krill is shown below in Table 44:

TABLE 44

Typical Mass Balance Of Antarctic Krill

| Matter | From 500 kg raw krill + water | Dry weight |
| --- | --- | --- |
| Wet PPC material | 80 kg | 28% |
| PPC meal | 25 kg | 97% |
| Hydrolysate | 770 kg | 6% |
| CHF | 78 kg | 60% |

TABLE 44-continued

Typical Mass Balance Of Antarctic Krill

| Matter | From 500 kg raw krill + water | Dry weight |
|---|---|---|
| Fluoride-containing particles | 45 kg | 40% |
| Neutral oils | <5 kg | |

The fluoride content in the hydrolyzed and disintegrated krill material is 1.2 g/kg, whereas in the PPC it is at most 0.5 g/kg and typically 0.3 g/kg. Thus, about two thirds of the fluoride has been removed.

In one embodiment, the present invention contemplates a krill powder derived from Antarctic krill (*Euphausia superba*). Generally, the krill powder comprises a reddish powder that is rich in marine omega-3 phospholipids, proteins, peptides and astaxanthin (particle size: 80 mesh<250 micron). When the krill powder is stored in the dark between approximately 2-8° C. in sealed foil bags (e.g., 25 kg each) with an inert gas headspace, covered by a cardboard carton and a plastic inner liner the powder remains stable for at least two years. The krill powder may have the following exemplary analytical specifications. See, Table 45

TABLE 45

Analytical Specifications Of An Exemplary Krill Powder

| Parameter | Method | Limit | Unit |
|---|---|---|---|
| Moisture | NIR | max 6 | % |
| Fat | NIR | min 25 | % |
| Protein (N * 6.25) | NIR | min 55 | % |
| Ash | NIR | max 10 | % |
| Phospholipids (% of total fats) | NIR | min 40 | % fat |
| EPA C20:5 n-3 (expressed as FFA) | GC/AM-OLY-01 | min 25 | mg/g |
| DHA C22:6 n-3 (expressed as FFA) | GC/AM-OLY-01 | min 15 | mg/g |
| Total omega-3 (expressed as FFA) | GC/AM-OLY-01 | min 50 | mg/g |
| Total aerobic count (TAC, 35° C., 48 h) | APHA 2001 4th Ed Ch 7 | <5.0 × $10^4$ | cfu/g |
| *Clostridium Perfringens* | APHA 2001 4th Ed Ch 34 | <500 | cfu/g |
| *Staphylococcus Aureus* | APHA 2001 4th Ed Ch 39 | <10 | cfu/g |
| *Escherichia Coli* | APHA 2001 4th Ed Ch 8 | <3 | mpn/g |
| *Salmonella* | ISO6579 | Not detected | per 25 g |
| Yeast and mould | APHA 2001 4th Ed Ch 10.5 mod | <1000 | Cfu/g |
| In-organic Arsenic | External | max 0.1 | mg/kg |
| Cadmium (Cd) | External | max 0.3 | mg/kg |
| Mercury (Hg) | External | max 0.01 | mg/kg |
| Lead (Pb) | External | max 0.03 | mg/kg |
| PCDD/PCDF (WHO-TEQ) | External | max 2.0 | pg/g |
| Dioxinlike PCBs (WHO-TEQ) | External | max 3.0 | pg/g |
| Benzo(a)pyrene | External | max 2.0 | ng/g |

The exemplary krill powder may also have the following fatty acid composition. See, Table 46.

TABLE 46

Fatty Acid Analysis Of An Exemplary Krill Powder

| 14:0 | g/100 g extracted fat | 7.5 |
|---|---|---|
| 16:0 | g/100 g extracted fat | 16.4 |
| 18:0 | g/100 g extracted fat | 0.9 |
| 20:0 | g/100 g extracted fat | <0.1 |
| 22:0 | g/100 g extracted fat | <0.1 |
| 16:1 n-7 | g/100 g extracted fat | 3 |
| 18:1 (n-9) + (n-7) + (n-5) | g/100 g extracted fat | 13.0 |
| 20:1 (n-9) + (n-7) | g/100 g extracted fat | 0.8 |
| 22:1 (n-11) + (n-9) + (n-7) | g/100 g extracted fat | 0.4 |
| 24:1 n-9 | g/100 g extracted fat | <0.1 |
| 16:2 n-4 | g/100 g extracted fat | 0.4 |
| 16:3 n-4 | g/100 g extracted fat | 0.2 |
| 18:2 n-6 | g/100 g extracted fat | 1.3 |
| 18:3 n-6 | g/100 g extracted fat | 0.2 |
| 20:2 n-6 | g/100 g extracted fat | 0.1 |
| 20:3 n-6 | g/100 g extracted fat | 0.1 |
| 20:4 n-6 | g/100 g extracted fat | 0.2 |
| 22:4 n-6 | g/100 g extracted fat | <0.1 |
| 18:3 n-3 | g/100 g extracted fat | 1.8 |
| 18:4 n-3 | g/100 g extracted fat | 4.6 |
| 20:3 n-3 | g/100 g extracted fat | 0.2 |
| 20:4 n-3 | g/100 g extracted fat | 0.4 |
| 20:5 n-3 | g/100 g extracted fat | 13.5 |
| 21:5 n-3 | g/100 g extracted fat | 0.6 |
| 22:5 n-3 | g/100 g extracted fat | 0.3 |
| 22:6 n-3 | g/100 g extracted fat | 7.8 |

The exemplary krill powder may also have the following mass balance composition. See, Table 47.

TABLE 47

Mass Balance Composition Of An Exemplary Krill Powder

| Fat | % | 30.2 |
|---|---|---|
| Crude protein | % | 61.1 |
| Moisture | % | 4.4 |
| Ash | % | 5.5 |
| Salt | % | 1.7 |
| Astaxanthin | mg/kg | 52 |

The exemplary krill powder may also have the following amino acid composition. See, Table

TABLE 48

Amino Acid Composition Of An Exemplary Krill Powder

| Aspartic acid | g/100 g sample | 6.06 |
|---|---|---|
| Glutaminic acid | g/100 g sample | 7.23 |
| Hydroxyproline | g/100 g sample | <0.01 |
| Serine | g/100 g sample | 2.75 |
| Glycine | g/100 g sample | 2.68 |
| Histidine | g/100 g sample | 1.28 |
| Arginine | g/100 g sample | 3.96 |
| Threonine | g/100 g sample | 3.36 |
| Alanine | g/100 g sample | 3.08 |
| Proline | g/100 g sample | 2.49 |
| Tyrosine | g/100 g sample | 2.97 |
| Valine | g/100 g sample | 3.86 |
| Methionine | g/100 g sample | 2.01 |
| Isoleucine | g/100 g sample | 4.11 |
| Leucine | g/100 g sample | 5.67 |
| Phenylalanine | g/100 g sample | 3.45 |
| Lysine | g/100 g sample | 4.48 |

The exemplary krill powder may also have the following lipid composition. See, Table 49.

TABLE 49

Lipid Composition Of An Exemplary Krill Powder

| Triacylglycerol | g/100 g extracted fat | 39 |
|---|---|---|
| Diacylglycerol | g/100 g extracted fat | 0.6 |
| Monoacylglycerol | g/100 g extracted fat | <1 |
| Free fatty acids | g/100 g extracted fat | 3.8 |

TABLE 49-continued

| Lipid Composition Of An Exemplary Krill Powder | | |
|---|---|---|
| Cholesterol | g/100 g extracted fat | 1.8 |
| Cholesterol esters | g/100 g extracted fat | <1 |
| Phosphatidylethanolamine | g/100 g extracted fat | 0.05 |
| Phosphatidylinositol | g/100 g extracted fat | <1 |
| Phosphatidylserine | g/100 g extracted fat | <1 |
| Phosphatidylcholine | g/100 g extracted fat | 30 |
| Lyso-phosphatidylcholine | g/100 g extracted fat | 1.9 |

In one embodiment, the present invention contemplates a krill powder derived from Antarctic krill (*Euphausia superba*) that is commerically available under the trademark of RIMFROST PRISTINE. In one embodiment, the RIMFROST PRISTINE krill powder has the following fatty acid profile. See Table 50.

TABLE 50

| Fatty Acid Composition of RIMFROST PRISTINE. | |
|---|---|
| Fatty Acid Component | Quantitation |
| C14:0% | 9.30% |
| C14:0 mg/100 g | 1435.20 mg/100 g |
| C15:0% | 0.36% |
| C15:0 mg/100 g | 54.98 mg/100 g |
| C16:0% | 21.77% |
| C16:0 mg/100 g | 3360.74 mg/100 g |
| C18:0% | 1.24% |
| C18:0 mg/100 g | 190.66 mg/100 g |
| C20:0% | <LOQ % |
| C20:0 mg/100 g | <LOQ mg/100 g |
| C22:0% | <LOQ % |
| C22:0 mg/100 g | <LOQ mg/100 |
| C24:0% | <LOQ % |
| C24:00 mg/100 g | <LOQ mg/100 g |
| C16:1n-9% | 0.20% |
| C16:1n-9 mg/100 g | 31.53 mg/100 g |
| C16:1n-7 Palmitoleic | 4.18% |
| C16:1n-7 mg/100 g | 645.73 mg/100 g |
| C18:1n-9 Oleic | 10.35%/100 g |
| C18:1n-9 mg/100 g | 1597.33 mg/100 g |
| C 18:1 n-7% | 6.82% |
| C18:1n-7 mg/100 g | 1052.00 mg/100 g |
| C20:1n-11% | 0.31% |
| C20:1n-11 mg/100 g | 48.23 mg/100 g |
| C20:1n-9% | 0.73% |
| C20:1n-9 mg/100 g | 112.78 mg/100 g |
| C20:1n-7% | 0.34% |
| C20:1n-7 mg/100 g | 51.79 mg/100 g |
| C22:1n-11% | <LOQ % |
| C22:1n-11 mg/100 g | <LOQ mg/100 g |
| C22:1n-9% | 0.60% |
| C22:1n-9 mg/100 g | 92.33 mg/100 g |
| C24:1n-9% | 0.17% |
| C24:1n-9 mg/100 g | 26.27 mg/100 g |
| C18:2n-6 Linoleic | 1.78% |
| C18:2n-6 mg/100 g | 275.10 mg/100 g |
| C18:3n-6 Gamma Linolenic | 0.15% |
| C18:3n-6 mg/100 g | 23.08 mg/100 g |
| C 20:2 n-6 | 0.10% |
| C 20:2n-6 mg/100 g | 15.76 mg/100 g |
| C 20:3 n-6 | 0.07% |
| C20:3n-6 mg/100 g | 10.51 mg/100 g |
| C20:4n-6 Eicosatetraenoic | 0.29% |
| C20:4n-6 mg/100 g | 44.47 mg/100 g |
| C22:4n-6 Docosatetraenoic | 0.06% |
| C22:4n-6 mg/100 g | 9.38 mg/100 g |
| C22:5n-6 Docosapentaenoic (DPA) | <LOQ % |
| C22:5n-6 mg/100 g | <LOQ mg/100 g |
| C18:3n3 Linolenic Acid | 2.71% |
| C18:3n-3 mg/100 g | 418.85 mg/100 g |
| C18:4n-3 | 6.78% |
| C18:4n-3 mg/100 g | 1047.12 mg/100 g |
| C20:3n-3 Eicosatrienoic | 0.29% |
| C20:3n-3 mg/100 g | 44.29 mg/100 g |

TABLE 50-continued

| Fatty Acid Composition of RIMFROST PRISTINE. | |
|---|---|
| Fatty Acid Component | Quantitation |
| C20:4n-3 | 0.49% |
| C20:4n-3 mg/100 g | 75.63 mg/100 g |
| C20:5 n 3 EPA | 17.73% |
| C20:5n-3 mg/100 g | 2737.16 mg/100 g |
| C21:5n-3 Heneicosapentaenoic | 0.68% |
| C21:5n-3 mg/100 g | 105.28 mg/100 g |
| C22:5 (cis-7,10,13,16,19)-Docosapentaenoic acid | 0.41% |
| C22:5n-3 mg/100 g | 63.80 mg/100 g |
| C22:6n-3 DHA. | 10.32% |
| C22:6n-3 mg/100 g | 1592.83 mg/100 g |
| C16:02% | 0.54% |
| C16:02 mg/100 g | 83.13 mg/100 g |
| C16:03% | 0.25% |
| C16:03 mg/100 g | 38.47 mg/100 g |
| C16:04% | 0.97% |
| C16:04 mg/100 g | 150.31 mg/100 g |
| Total PUFA % | 43.64% |
| Total PUFA mg/100 g | 6735.18 mg/100 g |
| Total Fatty Acids | 100.00% |
| Total mg/100 g | 15434.74 mg/100 g |
| Total Saturated Fatty Acids | 32.66% |
| Total saturated Fatty acids mg/100 g | 5041.58 mg/100 g |
| Total monounsaturated % | 23.70% |
| Total monounsaturated mg/100 g | 3657.99 mg/100 g |
| Total n-6 PUFA % | 2.45% |
| Total n-6 PUFA mg/100 g | 378.32 mg/100 g |
| Total n-3 PUFA | 39.42% |
| Total n-3 PUFA mg/100 g | 6084.95 mg/100 g |

LOQ = limit of quantification

In one embodiment, the RIMFROST PRISTINE krill powder also has the following additional components. See Table 51.

TABLE 51

| Additonal Components of RIMFROST PRISTINE | |
|---|---|
| Component | Quantitation |
| Carbohydrates | 0.6 g/100 g |
| Dietary Fiber | 3.6 g/100 g |
| Crude Protein Kjeldahl (N × 6.25) | 63.1 g/100 |
| Salt (calc. from sodium) | 1.98 g/100 g |
| Sodium (Na) | 7900 mg/kg |
| Moisture | 5.01 g/100 g |

V. Nutraceutical/Pharmaceutical Compositions

The present invention further provides nutraceutical and/or pharmaceutical compositions (e.g., comprising the compounds described above). The nutraceutical/pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Nutraceutical/pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 μg to 100 g per kg of body weight, once or more daily, to once every 20 years.

EXPERIMENTAL

Example I

Clinical Trial of Krill Powder Administration to Hypertensive Patients

This example provides a prospective, randomized, single-center, double-blinded, placebo-controlled study on safety and tolerability of the krill powder product in slightly obese study subjects with moderately elevated blood pressure.

The krill powder used in this trial comprised a reddish powder derived from Antarctic Krill (*Euphausia superba*) that is rich in marine omega-3 phospholipids, proteins, peptides and astaxanthin.

The study was a randomised, double-blinded, placebo-controlled intervention study with the slightly obese subjects with mildly or moderately elevated blood pressure. In total n=60 subjects was randomised according to randomisation list to two groups (krill powder or placebo) in a balanced manner (1:1), separately for both gender. Follow-up period was 8-weeks and study duration with an enrolment phase up to 10 weeks.

Example II

Statistics

All study data was summarised using descriptive statistics. Descriptive statistics includes observations such as the number of observations, mean, standard deviation, standard error, minimum, median and maximum for the variables in continuous scale. The primary variable, number of reported adverse events in the krill powder and placebo groups, was compared descriptively and using a Poisson regression model suitable for analysing count data.

The statistical analyses will be summarised in detail in separate statistical analysis plan which includes a list of tables. All study data will summarised using descriptive statistics. Descriptive statistics will include number of observations, mean, standard deviation, standard error, minimum, median and maximum for the variables in continuous scale. For dichotomous and other variables in classified scale number of observation and percentages will be presented.

Statistical Analysis

For the statistical analyses, an evaluation of the assumptions was done. If deviations from normality was observed, a corresponding non-parametric model was applied to ensure the correctness of conclusion. A two-sided p-value of 0.05 or below is considered as statistically significant.

Baseline Characteristics and Safety Variables

Baseline characteristics were summarised using descriptive statistics. Safety variables other than the primary parameters were summarised also descriptively. Adverse events were reported by system organ class and preferred term (MedDRA coded) as well as by severity, seriousness and causality. SAEs were presented in a separate listing.

Primary and Secondary Analysis

The primary variable, number of reported adverse events in the study groups were compared descriptively and by using a Poisson regression model suitable for analysing count data. Incidences were also compared using risk difference and corresponding 95% confidence interval.

Blood pressure values and laboratory parameters were summarised for both groups descriptively at each measurement point including the changes from baseline. Changes from baseline between the study groups were compared using an analysis of covariance models adjusting for baseline values.

Sample Size

This study comprised a sample size where approximately 75% power was achieved to show that the rate of AEs in the active group is less than double than in the placebo group (i.e. the 95% upper confidence limit for the rate ratio being lower than 2). This calculation was based on the assumption that the mean number of AEs is 1 per subject in each group using the Poisson distribution.

Example III

Determination of Fluoride Content

This example presents one method of determining fluoride content of krill products as fluoride by chemical analysis using an ion selective electrode.

The data demonstrate that by removing the exoskeleton in the process of producing krill meal, the fluoride content of the meal and the oil produced from the meal have a markedly reduced fluoride content. See, Table II.

TABLE II

Fluoride Content Comparison To Conventional Processes

| | Process of present invention | Conventional process |
|---|---|---|
| Krill Powder | 300-500 ppm | 1300 ppm |

REFERENCES

Andersson C, Lyass A, Vasan R S, Massaro J M, D'Agostino R B Sr, Robins S J. Long-term risk of cardiovascular events across a spectrum of adverse major plasma lipid combinations in the Framingham Heart Study. Am Heart J. 2014; 168:878-883.

Berge K, Musa-Veloso K, Harwood M, Hoem N, Burri L. Krill oil supplementation lowers serum triglycerides without increasing low-density lipoprotein cholesterol in adults with borderline cholesterol in adults with borderline high or high triglyceride levels. Nutrition Research 2014; 34:126-133.

Bunea R, Farrah K E, Deutsch L. Evaluation of the effect of Neptune krill oil on the clinical course of hyperlipidemia. Altern Med Rev 2004; 9:420-428.

Calder P C. n-3 polyunsaturated fatty acids and cytokine production in health and disease. Ann Nutr Metab 1997; 41:203-234.

Calder P C. Dietary modification of inflarmnation with lipids. Proc Nutr Soc 2002; 61:345-358.

Ciccone M M, Cortese F, Gesualdo M, Carbonara S, Zito A, Ricci G, De Pascalis F, Scicchitano P, Riccioni G. Dietary intake of carotenoids and their antioxidant and anti-inflammatory effects in cardiovascular care. Mediators of Inflammation 2013. Article ID 782137, 11 pages, http://dx.doi.org/10.1155/2013/782137

Fassett R, Coombes J S. Astaxanthin in cardiovascular health and disease. Molecules 2012; 17:2030-2048.

Guerin M, Huntley M E, Olaizola M. *Haematococcus astaxanthin*: applications for human health and nutrition. Trends Biotechnol. 2003 May; 21:210-216.

Harnedy P A, FitzGerald R J. Cardioprotective peptides from marine sources. Curr Protein Pept Sci. 2013; 14:162-172.

Harris W S. Omega-3 fatty acids and cardiovascular disease: a case for omega-3 index as a new risk factor. Pharmacol Res 2007; 55:217-223.

Hatanaka A, Miyahara H, Suzuki K I, Sato S. Isolation and identification of antihypertensive peptides from antarctic krill tail meat hydrolysate. J Food Sci. 2009; 74: doi: 10.1111/j.1750-3841.2009.01138.x.

Harris W S, Dayspring T D, Moran T J. Omega-3 fatty acids and cardiovascular disease: new developments and applications. Postgrad Med. 2013; 125:100-113.

Krill oil monograph. Alternative Medicine Review 2010; 15:84-86.

Lee J K, Jeon J K, Kim S K, Byun H G. Characterization of bioactive peptides obtained from marine invertebrates. Adv Food Nutr Res. 2012; 47-72.

Li K, Huang T, Zheng J, Wu K, Li D. Effect of marine-derived n-3 polyunsaturated fatty acids on C-reactive protein, interleukin 6 and tumor necrosis factor α: a meta-analysis. PLOS ONE 2014; 9, e88103. DOI: 10.1371/journal.pone.0088103.

Martinez-Maqueda D, Miralles B, Recio I, Hernmndez-Ledesma B. Antihypertensive peptides from food proteins: a review. Food Funct. 2012; 3:350-361.

Oh P C, Koh K K, Sakuma I, Lim S, Lee Y, Lee S, Lee K, Han S H, Shin E K. Omega-3 fatty acid therapy dose-dependently and significantly decreased triglycerides and improved flow-mediated dilation, however, did not significantly improve insulin sensitivity in patients with hypertriglyceridem-ia. Nit J Cardiol. 2014; 176:696-702.

Riccioni G, D'Orsazio N, Franceschelli S, Speranza L. Marine carotenoids and cardiovascular risk markers. Mar. Drugs 2011; 9:1166-1175.

Sadzuka Y, Sugiyama I, Miyashita M, Ueda T, Kikuchi S, Oshiro E, Yano A, Yamada H. Beneficial effects by intake of *Euphausiacea pacifica* on high-fat diet-induced obesity. Biol Pharm Bull 2012; 35:568-572.

Trepanowski J F, Kabir M M, Alleman R J, Bloomer R J. A 21-day Daniel fast with or without krill oil supplementation improves anthropometric parameters and the cardiometabolic profile in men and women. Nutrition & Metabolism 2012; 9:82-88.

von Schacky C. The omega-3 index as a risk factor for cardiovascular diseases. Prostaglandins Other Lipid Mediat 2011; 96:94-98.

von Schacky C, Harris W S. Cardiovascular benefits of omega-3 fatty acids. Cardiovasc Res 2007; 73:310-315.

Wachira J K, Larson M K, Harris W S. n-3 Fatty acids affect haemostasis but do not increase the risk of bleeding: clinical observations and mechanistic insights. Br J Nutr. 2014; 111:1652-1662.

I claim:

1. A method, comprising:
   a) providing;
      i) a patient exhibiting at least one prehypertensive symptom; and
      ii) an effective amount of a krill powder composition;
   b) administering said krill powder composition to said patient under conditions such that said at least one prehypertensive symptom is reduced without altering triglyceride levels.

2. The method of claim 1, wherein said at least one prehypertensive symptom comprises a diastolic blood pressure ranging between approximately 86-90 mmHg.

3. The method of claim 1, wherein said at least one prehypertensive symptom comprises a systolic blood pressure ranging between approximately 138-142 mmHg.

4. The method of claim 1, wherein said reduced at least one prehypertensive symptom comprises an approximate 3% reduction in diastolic blood pressure.

5. The method of claim 1, wherein said reduced at least one prehypertensive symptom comprises an approximate 5% reduction in systolic blood pressure.

6. The method of claim 1, wherein said patient is overweight having a body mass index ranging between approximately 25.0 to 29.9.

7. The method of claim 1, wherein said patient is obese having a body mass index ranging between approximately 30.0-39.9.

8. The method of claim 1, wherein said patient is extremely obese having a body mass index in exess of 40.0.

9. The method of claim 1, wherein said krill powder comprises between approximately 300-400 ppm fluoride.

10. The method of claim 1, wherein said krill powder comprises a reddish color.

11. The method of claim 1, wherein said effective amount of said krill powder remains stable over a one year period.

12. The method of claim 1, wherein said conditions comprise an approximate 50% reduction in adverse events within said patient as compared to a subject not administered said effective amount of krill powder.

13. The method of claim 1, wherein said conditions comprise no significant changes in said patient's laboratory measurements selected from the group consisting of low density lipoprotein levels, high density lipoprotein levels, total cholesterol levels, and triglyceride levels.

14. The method of claim 1, wherein said conditions comprise no significant changes in body weight of said patient.

15. The method of claim 1, wherein said krill powder is rich in marine omega-3 phospholipids, proteins, peptides and astaxanthin.

16. The method of claim 1, said krill powder is Antartic krill powder.

17. The method of claim 1, wherein said Antartic krill powder is *Euphanasia superba* krill powder.

* * * * *